United States Patent
Keenan

(10) Patent No.: US 7,472,153 B1
(45) Date of Patent: Dec. 30, 2008

(54) METHOD FOR EXPLOITING BIAS IN FACTOR ANALYSIS USING CONSTRAINED ALTERNATING LEAST SQUARES ALGORITHMS

(75) Inventor: Michael R. Keenan, Albuquerque, NM (US)

(73) Assignee: Sandia Corporation, Albuquerque, NM (US)

( * ) Notice: Subject to any disclaimer, the term of this patent is extended or adjusted under 35 U.S.C. 154(b) by 834 days.

(21) Appl. No.: 10/794,538

(22) Filed: Mar. 4, 2004

(51) Int. Cl.
  *G06F 7/38* (2006.01)
  *G01N 31/00* (2006.01)

(52) U.S. Cl. .................... 708/446; 702/23

(58) Field of Classification Search ............ 708/446, 708/520, 607; 702/22, 23
  See application file for complete search history.

(56) References Cited

U.S. PATENT DOCUMENTS

| | | | |
|---|---|---|---|
| 6,584,413 B1 | 6/2003 | Keenan et al. | |
| 6,675,106 B1 | 1/2004 | Keenan et al. | |
| 6,687,620 B1 * | 2/2004 | Haaland et al. | 702/22 |
| 2005/0183958 A1 * | 8/2005 | Wikiel et al. | 205/82 |

OTHER PUBLICATIONS

BRO, Chemometrics and Intelligent Laboratory Systems, 1997, 38, 149-171.
Tauler, Analytical Chemistry, 1993, 65, 2040-2047.
Andrew, Applied Spectroscopy, 1998, 52, 6, 797-807.
Kotula, Microscopy and Microanalysis, 9 (1), 1 (2003).
Bro, Journal of Chemometrics, vol. 11, 393-401, (1997).
Hoerl, Technometrics, vol. 12, No. 1, 55-67, (Feb. 1970).
Marquardt, Technometrics, vol. 12, No. 3, 591-612, (Aug. 1970).
Wang, Analytica Chimica Acta, 476, (2003), 93-109.
Gemperline, Analytical Chemistry, vol. 75, No. 16, 4236-4243, (Aug. 2003).
Lawson, Solving Least Square Problems, 1995; Society for Industrial and Applied Mathematics, Philadelphia.
Bjorck, Numerical Methods for Least Squares Problems, 1996, Society for Industrial and Applied Mathematics, Philadelphia.
Draper, Applied Regression Analysis, Third Edition, 1998, A Wiley-Interscience Publication, New York.
U.S. Appl. No. 10/772,805, filed Feb. 4, 2004, Keenan.
U.S. Appl. No. 10/772,548, filed Feb. 4, 2004, Keenan.

* cited by examiner

*Primary Examiner*—Chuong D Ngo
(74) *Attorney, Agent, or Firm*—Kevin W. Bieg

(57) ABSTRACT

Bias plays an important role in factor analysis and is often implicitly made use of, for example, to constrain solutions to factors that conform to physical reality. However, when components are collinear, a large range of solutions may exist that satisfy the basic constraints and fit the data equally well. In such cases, the introduction of mathematical bias through the application of constraints may select solutions that are less than optimal. The biased alternating least squares algorithm of the present invention can offset mathematical bias introduced by constraints in the standard alternating least squares analysis to achieve factor solutions that are most consistent with physical reality. In addition, these methods can be used to explicitly exploit bias to provide alternative views and provide additional insights into spectral data sets.

26 Claims, 25 Drawing Sheets

US 7,472,153 B1

METHOD FOR EXPLOITING BIAS IN FACTOR ANALYSIS USING CONSTRAINED ALTERNATING LEAST SQUARES ALGORITHMS

STATEMENT OF GOVERNMENT INTEREST

This invention was made with Government support under contract no. DE-AC04-94AL85000 awarded by the U.S. Department of Energy to Sandia Corporation. The Government has certain rights in the invention.

FIELD OF THE INVENTION

The present invention relates to multivariate statistical techniques and, in particular, to a method for exploiting bias in factor analysis using constrained alternating least squares algorithms.

BACKGROUND OF THE INVENTION

Bias plays an important role in factor analysis and we often implicitly make use of it. The application of non-negativity constraints in alternating least squares (ALS) procedures, for instance, is nothing more than a statement that we are biased toward factor solutions that conform to physical reality. We are willing to accept a model that provides a poorer mathematical fit to the data in return for model that is easier to interpret in physical terms. When components are collinear, a large range of solutions may exist that satisfy the basic constraints and fit the data equally well. In such cases, the introduction of mathematical bias through the application of constraints may select solutions that are less than optimal. Peak shapes may be distorted, for example, or physically discrete chemical phases may appear to be mixed.

The biased ALS (BALS) algorithms of the present invention are designed to offset mathematical bias introduced by constraints in ALS with the goal of achieving factor solutions that are most consistent with physical reality. Methods are also described that are explicitly intended to exploit bias to provide alternative views and provide additional insights into spectral data sets.

SUMMARY OF THE INVENTION

The present invention is directed to a biased alternating least squares algorithm for factoring a data matrix into a product of a first factor matrix and a second factor matrix. An initial feasible estimate is made for a first factor matrix. The first factor matrix is normalized. A first bias parameter is selected and a least squares estimate is obtained for the first factor matrix, subject to constraints on the first factor matrix. A second bias parameter is selected and a least squares estimate is obtained for the second factor matrix, subject to constraints on the second factor matrix. The process of obtaining biased alternating least squares estimates is repeated at least once, or until the estimates converge. Finally, an unbiased estimate of the first factor matrix is computed. The biased alternating least squares algorithm is particularly useful for the analysis of spectroscopic data, wherein the data matrix is factored into a factor matrix comprising estimated pure component spectra and a factor matrix comprising estimated component concentrations.

The data matrix can be preprocessed (e.g., weighted for heteroscedastic noise, spatially and/or spectrally compressed, etc.). The bias parameters preferably are selected to be between the smallest and largest eigenvalue of the crossproduct of the respective factor matrix, in order to increase or decrease the component contrast. The constraints on the factor matrices can comprise non-negativity, general linear equality constraints, general linear inequality constraints, or the like.

BRIEF DESCRIPTION OF THE DRAWINGS

The accompanying drawings, which are incorporated in and form part of the specification, illustrate the present invention and, together with the description, describe the invention. In the drawings, like elements are referred to by like numbers.

DETAILED DESCRIPTION OF THE INVENTION

Figure 1:
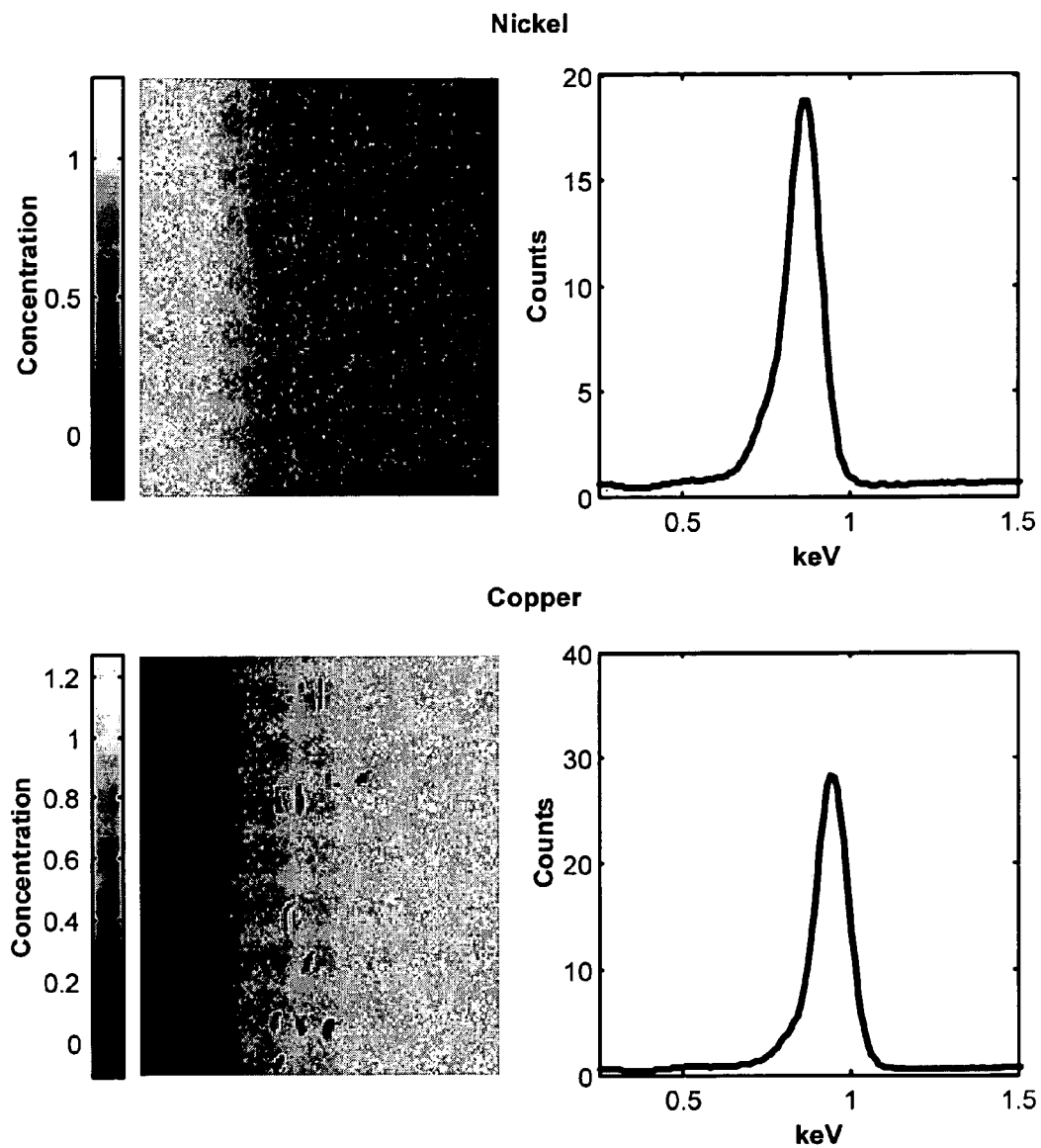
FIG. 1 shows the estimated concentration images from a classical least squares fit, using the measured pure component spectra, of an energy dispersive x-ray spectral (EDS) image of a copper/nickel diffusion couple.

Factor analysis comprises a family of multivariate statistical techniques that attempt to distill high-dimensional data into a limited number of components that retain the essential information pertinent to an underlying model. Factor analysis has a long history in the social sciences and has also proven effective for solving a variety of chemical problems. See, e.g., H. H. Harman, *Modern Factor Analysis*, The University of Chicago Press, Chicago (1976) and E. R. Malinowski, *Factor Analysis in Chemistry*, John Wiley & Sons, New York (2002).

In mathematical terms, factor analysis methods seek to decompose a data matrix D into a product of matrix factors that describe all of the relevant information contained in D in physically meaningful terms. For example, in a spectroscopic experiment which adheres to Beer's Law, D is an m×n matrix containing spectroscopic data (e.g. an n-channel spectrum at each of m pixels in a spectrum image) and we wish to estimate factor matrices C and S, which describe the concentrations and spectra, respectively, of the p pure components that comprise the sample. In this case, the data are said to follow a bilinear model:

$$D = CS^T \quad (1)$$

Higher order, multilinear models, have also found increasing use in recent years. See R. Bro, "PARAFAC. Tutorial and applications", *Chemometrics. Intell. Lab Syst.* 38(2), 149 (1997). In this case, a multidimensional data array $\underline{D}$ may be factored into a product of several matrices. A general multilinear model, for instance, might be written:

$$\underline{D} = f(A, B, C, \ldots) \quad (2)$$

where A, B, C, etc., are conformable matrices. The solution of Equation (2), however, is typically accomplished by reducing the problem to one of solving a series of bilinear models. Thus, methods for computing solutions to Equation (1) are of fundamental importance and will be the focus of this description.

It is well known, that factor-based methods suffer from "rotational ambiguity" and "intensity ambiguity", that is, there are an infinite number of factor models that will describe the data equally well. See Tauler et al., "Multivariate Curve Resolution Applied to Spectral Data from Multiple Runs of an Industrial process," *Anal. Chem.* 65(15), 2040 (1993). In practice, relatively unique solutions are obtained by applying constraints on the admissible solutions.

Principal Component Analysis (PCA), used either by itself or to preprocess data, is the most ubiquitous tool of factor analysis. In the spectroscopic context, the constraints imposed by PCA are that the concentration and spectral factors must contain orthogonal components and that the components serially maximize the variance in the data that each accounts for. Neither constraint has any physical basis; thus, the factors obtained via PCA are abstract and not easily interpreted. The PCA solution does have the useful property, however, that for a given number of factors p, it provides the best p-factor model for describing the data in a least squares sense.

The key to deriving easily interpretable components is to constrain the factor solutions to conform to physical reality. While we will not, in general, know either C or S in Equation (1), we may know some of their properties. Physically plausible concentrations and spectra, for instance, may be known a priori to be non-negative. A common way to impose such constraints is to solve the factor model in an iterative fashion as a series of constrained, conditional least squares problems. For the applications in multivariate image analysis, this approach has been described in detail. See J. J. Andrew et al., "Rapid Analysis of Raman Image Data Using Two-Way Multivariate Curve Resolution," *Appl. Spect.* 52(6), 797 (1998); P. Kotula et al., "Automated Analysis of SEM X-Ray Spectrum Images: A Powerful New Microanalysis Tool," *Microscopy and Microanalysis* 9(1), 1 (2003); U.S. Pat. No. 6,584,413 to Keenan and Kotula; and U.S. Pat. No. 6,675,106 to Keenan and Kotula, which are incorporated herein by reference.

There are many details that are specific to the particular problems at hand. At a basic level, however, the Multivariate Curve Resolution-Alternating Least Squares (MCR-ALS) procedure reduces to the algorithm:

Make an initial guess for S
Do until converged:
  1. normalize S  (3)
  2. solve $\min_c \|D^T - SC^T\|_F$ subject to constraints on C
  3. solve $\min_s \|D - CS^T\|_F$ subject to constraints on S Of course, the roles of C and S can be interchanged whereby an initial guess is made for C and the order of the least squares solution steps 2 and 3 is reversed. A normalization step 1 is needed to eliminate the "intensity" ambiguity in factor analysis. That is, without normalizing one of the factors to a constant magnitude, it would be possible for one factor to become arbitrarily large while the other factor becomes arbitrarily small without improving on the quality of the fit.

In the absence of constraints, the classical least squares (CLS) solution provides an unbiased estimate of the unknown parameters. Once constraints are applied, however, bias is introduced into the solution. Taking non-negativity constrained least squares (NNLS) as an example, the inequality constrained least squares problem with multiple observation vectors $[b_1\ b_2\ \ldots\ b_n]=B$ and coefficient matrix A can be written in generic terms as:

$$\hat{x} = \min_x \|AX - B\|_F^2 = \sum_{i=1}^n \min_{x_j} \|Ax_j - b_j\|_2^2 \text{ subject to } x_j \geq 0 \quad (4)$$

For example, in the algorithm described in Equation (3), B can be the data matrix D, A can be the factor matrix C or S, and X can be the complementary factor matrix S or C. The active/passive set method for estimating each column of $\hat{X}$ has been treated at length previously. See C. L. Lawson et al., *Solving Least Squares Problems, Classics in applied mathematics* 15, Society for Industrial and Applied Mathematics, Philadelphia (1995) and R. Bro et al., "A fast non-negativity-constrained least squares algorithm," *J. of Chemometrics* 11(5), 393 (1997), which are incorporated herein by reference.

In brief, the inequality constraints define a feasible region in multidimensional space. At the least squares minimum, variables will either reside in the interior of the feasible region or will be found on the boundary. The passive set comprises those variables that are interior to the feasible region, and the active set, those on the boundary. If we knew, a priori, the active set for the optimal solution, the solution to the inequality constrained least squares problem could be obtained as the solution to the equality constrained problem with all active-set variables being constrained to be equal to their boundary values. The active/passive set strategy for solving inequality constrained least squares problems, then, is to iteratively move variables between the active and passive sets in such a way that the sum of the squared residuals steadily decreases and feasibility of the solution is maintained. Since there are a limited number of ways to partition variables between the active and passive sets, this process is guaranteed to converge.

The fact that the constraints introduce bias into the least squares solution can be seen by extending the arguments of Chapter 20 of the C. L. Lawson et al. reference to show that the constrained estimate $\hat{x}_{NNLS}$ is a linear transformation of the classical least squares estimate $\hat{x}_{CLS}$:

$$\hat{x}_{NNLS}=K(AK)^+A\hat{x}_{CLS} \quad (5)$$

K is a p×k selection matrix where k is the number of the p total variables that are in the passive set, and the superscript + represents a pseudoinverse. The two estimates coincide only for the case that K is the identity matrix, namely, when no variables are actively constrained.

The manifestation of bias is best illustrated by a simple example. FIG. 1 shows the results of a CLS fit of the concentrations for an energy dispersive x-ray spectral image of a copper/nickel diffusion couple. Details of the sample and experiment are given in Kotula et al. In this case, regions of the sample at the far left and far right of the image are known to be pure nickel and pure copper, respectively. The pure component spectra were then obtained by simply averaging the measured spectra over the leftmost 16 columns of the image for nickel and over the rightmost 16 columns for copper. In the absence of noise, the concentrations of both nickel and copper should vary over the range from 0-1.

Figure 2:
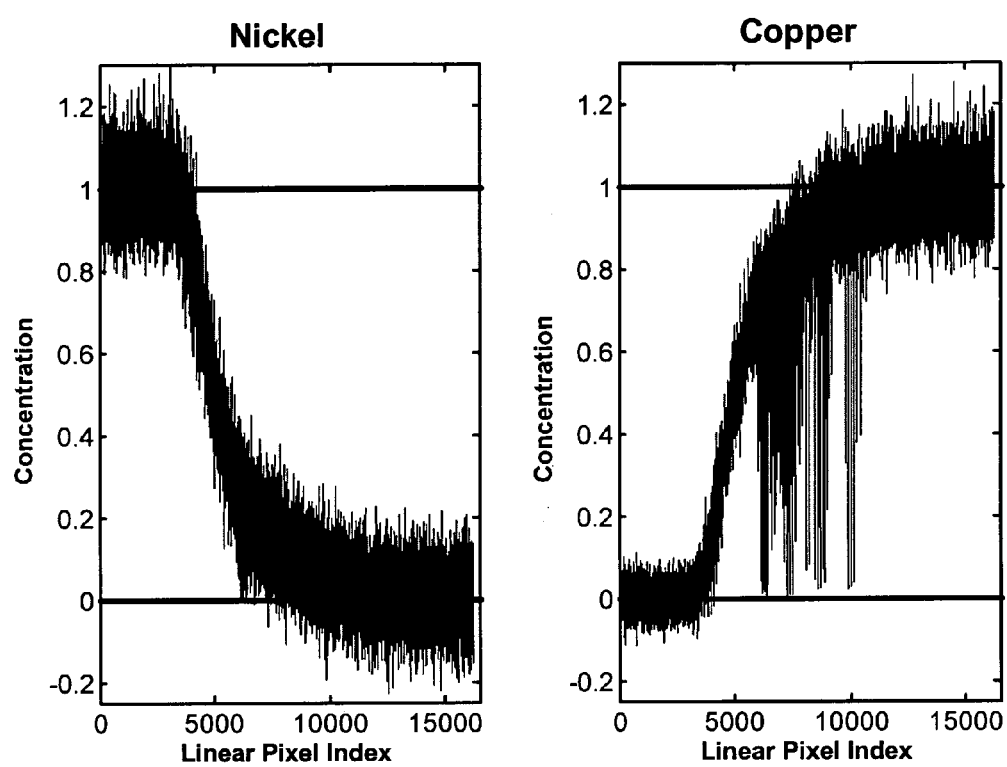
FIG. 2 shows the estimated concentrations of nickel and copper, computed using a classical least squares (CLS) algorithm, plotted against a linear pixel index computed columnwise.

FIG. 2 shows the estimated concentrations of nickel and copper plotted against a linear pixel index computed column-wise using the CLS algorithm. Due to noise, concentrations can both exceed one and go negative for some pixels. On average, however, the concentration of nickel is approximately one in the regions known to be pure nickel and approximately zero in the region known to be pure copper, with complementary results being obtained for copper.

Figure 3:
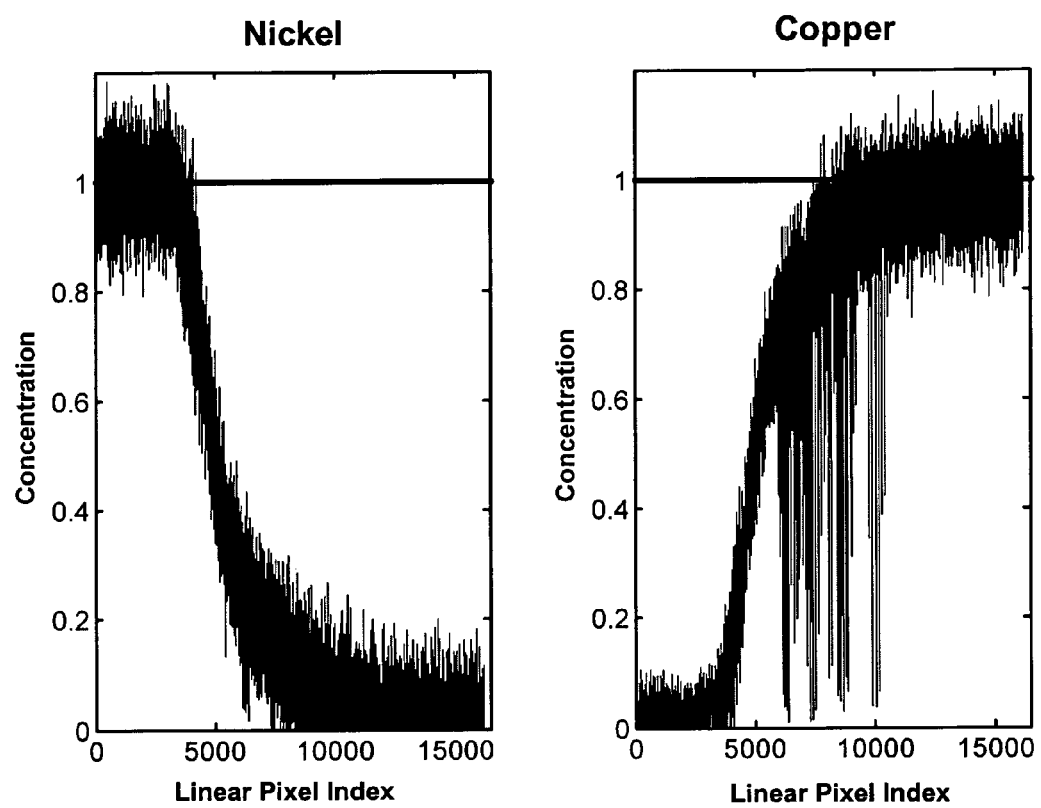
FIG. 3 shows the estimated concentrations of nickel and copper, computed using a non-negativity constrained least squares algorithm, plotted against a linear pixel index.

Applying non-negativity constraints, on the other hand, yields the results shown in FIG. 3. All concentrations are strictly non-negative but, on average, the estimated concentration of nickel is slightly positive in the region known to be pure copper and the estimated concentration of copper is slightly positive in the region known to be pure nickel. It is also evident that the concentrations of both nickel and copper are less than one in regions known to consist of the respective pure elements. Hence, the application of constraints is shown to introduce bias in the resulting estimates, and the specific effect is to narrow the range of the mean concentration estimates.

Figure 4:
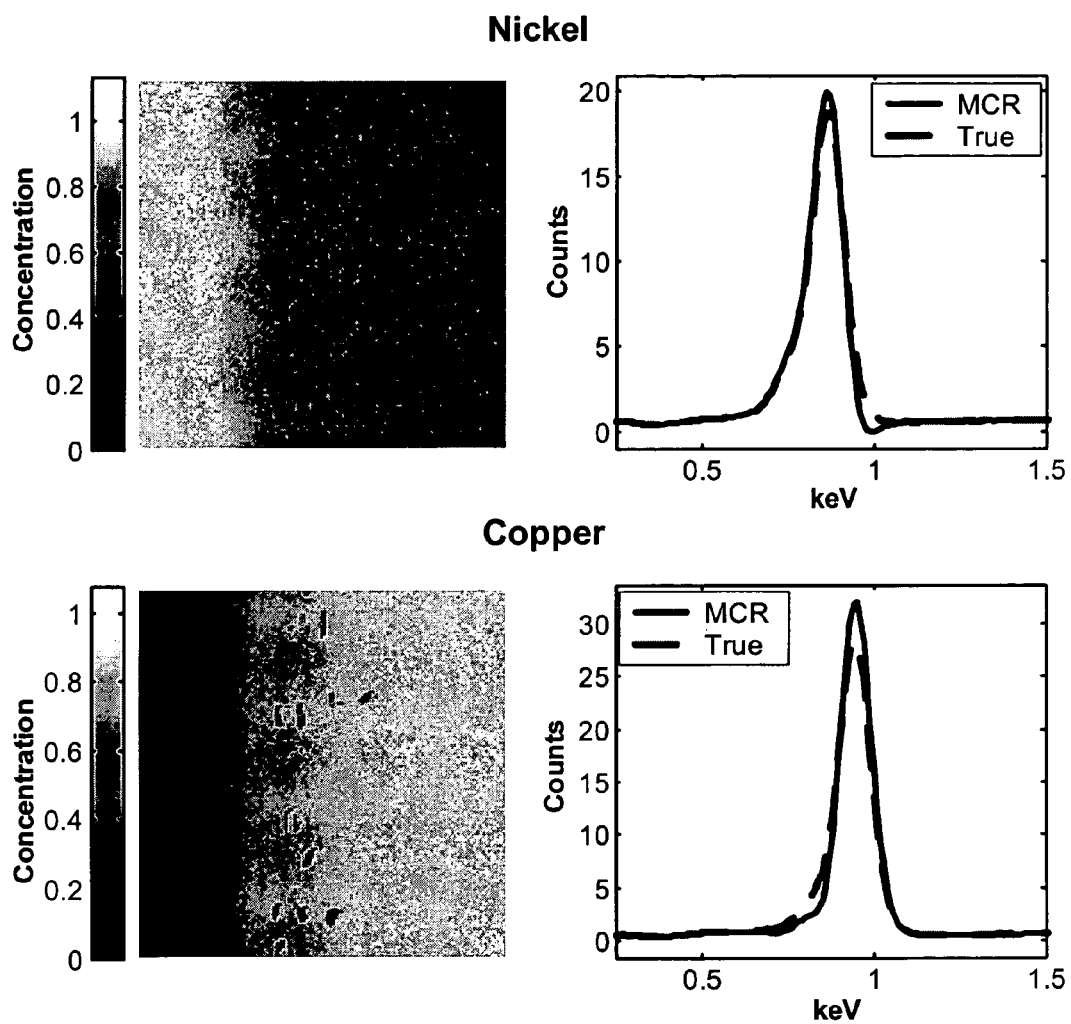
FIG. 4 shows the estimated concentration images and estimated pure-component spectra after complete convergence using a non-negativity constrained alternating least squares (ALS) algorithm.

While the bias is not too severe for a single NNLS solution, the effects are amplified in iterative algorithms, such as Equation (3). FIG. 4 shows the estimated pure-component spectra and concentration images after complete convergence of MCR-ALS for the copper/nickel data set. The known, true pure-component spectra were used to initialize the iteration, and both concentrations and spectra were constrained thereafter to be non-negative. Note, particularly in the case of copper, that the estimated pure-component spectra (labeled "MCR") have diverged from what is known to be true (labeled "True").

Figure 5A:
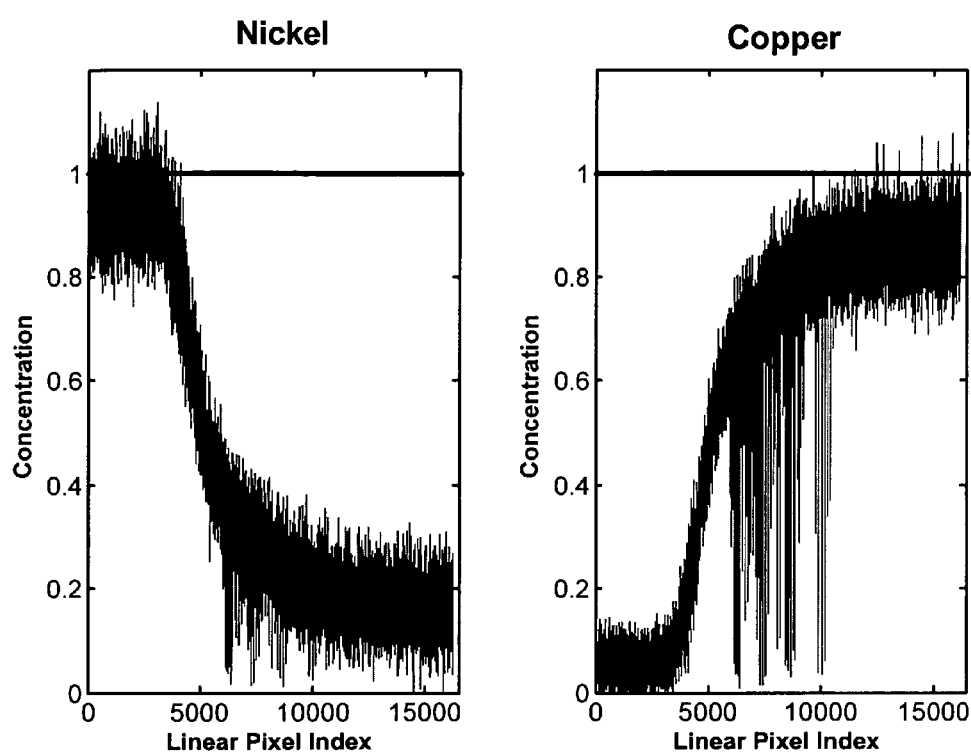
FIG. 5A shows the estimated concentrations of nickel and copper, computed using the non-negativity constrained ALS algorithm, plotted against a linear pixel index.
Figure 5B:
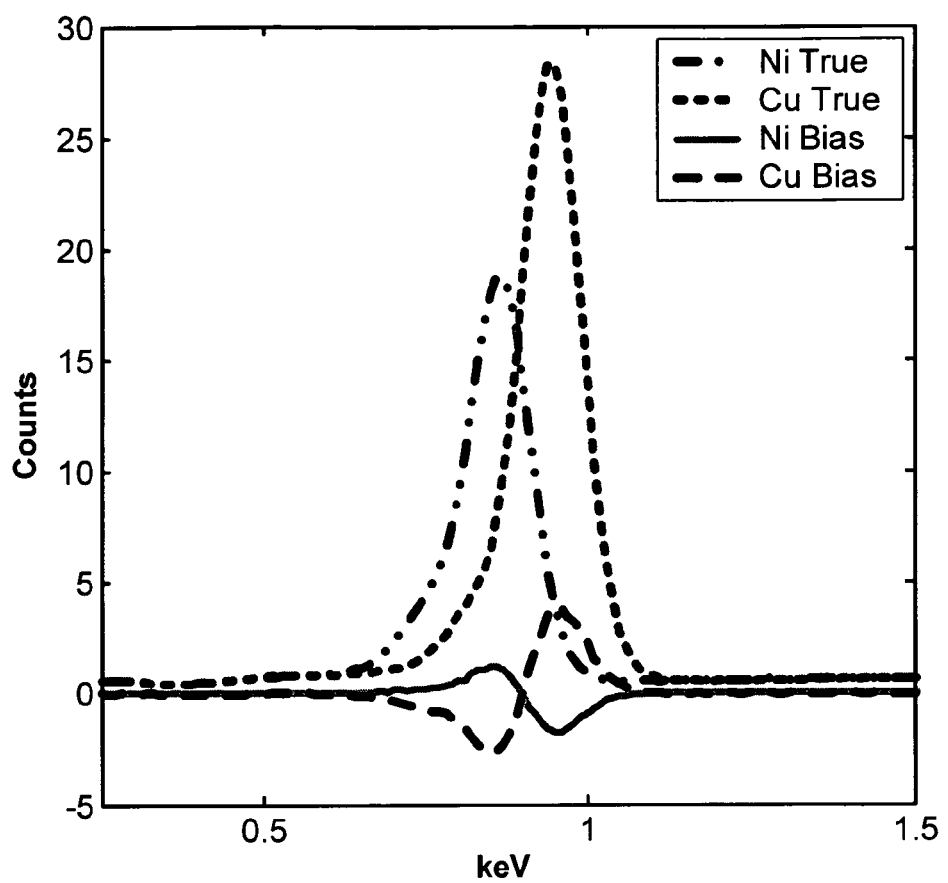
FIG. 5B shows the true pure component spectra and the bias introduced by the constrained ALS estimation of the pure component spectra.

A more telling look at the effect of bias on concentrations is shown in FIG. 5A. Regions known to be pure copper are estimated to be about 16% nickel! Interestingly, only a single concentration in this region is being actively constrained. Thus, lacking additional information, one would naturally assume that this portion of the sample is, in fact, a copper/nickel alloy rather than pure copper. The bias induced by constrained ALS into the pure-component spectral estimates has an opposing effect. Rather than showing apparent component mixing, the spectra are, in some sense, de-mixed. FIG. 5B compares the true nickel (labeled "Ni True") and copper (labeled "Cu True") spectra together with the bias in each estimate resulting from ALS (labeled "Ni Bias" and "Cu Bias", respectively). In spectral regions having relatively high nickel intensity, the ALS-estimated nickel component is enhanced and the copper component suppressed as compared to the true values. Conversely, copper intensity is enhanced and nickel intensity is suppressed in the channels having relatively high overall copper intensity. The maximum magnitude of the bias is about 15%.

Figure 6:
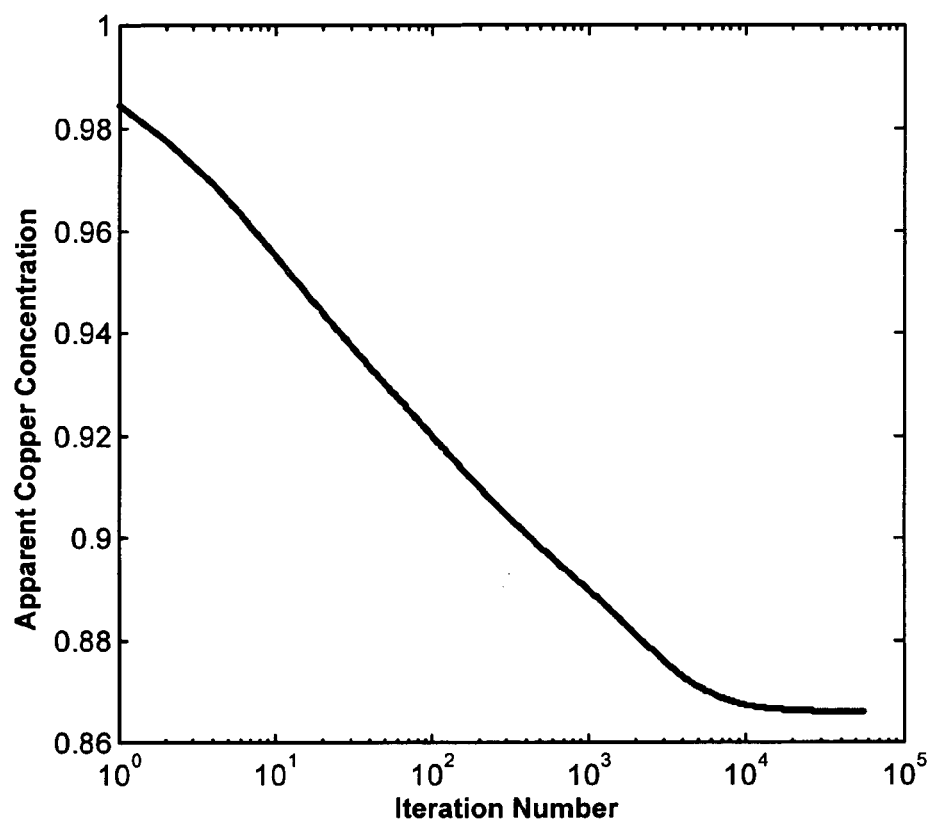
FIG. 6 shows the apparent mean copper concentration in the pure copper region as a function of the number of iterations, estimated using the non-negativity constrained ALS algorithm.

The origination and amplification of bias during constrained alternating least squares arises fundamentally from the asymmetric treatment of noise, and collinearity (i.e. non-orthogonality) of the pure components, either spectral, compositional, or both. In the foregoing example, positive biases in the zero-concentration regions result from the fact that apparent negative concentrations are suppressed, whereas, apparent positive concentrations are simply ignored. Consequently, known zero-concentration noise appears to have, on average, a positive concentration. The effect of positive concentration bias on fitting the data can be offset, in part, by biasing the corresponding pure spectral components in an opposite sense. These newly biased spectra then induce additional bias in the new concentration estimates, and so on. Since each iteration changes the bias only slightly, convergence to the constrained least squares minimum can be exceedingly slow. FIG. 6 shows the apparent mean copper concentration in the pure copper region as the ALS iteration proceeds. About 10,000 iterations are needed to achieve convergence; the process is slow, indeed.

Having established that constrained alternating least squares yields a biased estimate of the pure spectral and compositional components, we seek an alternative least squares solution process that enables us to offset the bias induced by the constraints. One approach is to employ biased least squares estimators at each step of the iteration. Two such estimators come to mind, Total Least Squares (TLS) and Ridge Regression (RR). See S. Van Huffel et al., *The Total Least Squares Problem*, Society for Industrial and Applied Mathematics, Philadelphia (1991); G. H. Golub et al., *Matrix Computations*, The John Hopkins University Press, Baltimore (1996); A. Bjorck, *Numerical Methods for Least Squares Problems*, Society for Industrial and Applied Mathematics, Philadelphia (1996); A. E. Hoerl et al., "Ridge Regression: Biased Estimation for Nonorthogonal Problems," *Technometrics* 12(1), 55 (1970); D. W. Marquardt et al., "Generalized Inverses, Ridge Regression, Biased Linear Estimation, and Nonlinear Estimation," *Technometrics* 12(3), 591 (1970); and N. R. Draper et al., *Applied Regression Analysis*, John Wiley & Sons, New York (1998), which are incorporated herein by reference.

The original motivation for developing these two techniques is quite different. TLS was developed to solve the "error-in-variables" problem. Classical least squares assumes that error is confined to the observations and that the least squares model itself (i.e. the data matrix A in Equation (4)) is error-free. TLS solves the problem for the case that the data as well as the observations are subject to error. RR, on the other hand, is intended to deal with difficulties associated with performing least squares estimates with highly collinear data (i.e. correlations among the columns of A). Clearly, both of these issues impact the ability of ALS to yield useful information. Under the assumptions of classical least squares, for instance, S is considered to be error-free while estimating C, and the resulting estimate of C will reflect any error present in the observations. In the following step, however, C is considered to be error-free when obtaining a new estimate for S. These assumptions are obviously inconsistent and, in fact, there is error in both S and C. Typical spectroscopic data can also exhibit a high degree of collinearity. Samples may consist of chemical mixtures having compositional collinearity and pure-component spectra often have overlapping spectral features giving rise to spectral collinearity.

As evidenced in the references, extensive theoretical work surrounds both TLS and RR. It is perhaps more fruitful, however, to simply consider the phenomenology of TLS and RR. The solution vectors obtained from the regression techniques considered here satisfy a set of normal equations that is unique to each:

TLS: $(A^TA - \sigma^2 I)x_{TSL} = A^Tb$

CLS: $A^TAx_{CLS} = A^Tb$

RR: $(A^TA + \lambda I)x_{RR} = A^Tb$ (6)

where I is the identity matrix. For TLS, the parameter $\sigma$ is the smallest singular value of the augmented matrix [A, b]. By the interlacing property of singular values, $0 < \sigma < \sigma_{min}$, where $\sigma_{min}$ is the smallest singular value of A (or, equivalently, $\sigma_{min}^2$ in is the smallest eigenvalue of $A^TA$). The key observation is that a small positive value is being subtracted from each element of the diagonal of $A^TA$. For RR, on the other hand, the ridge parameter $\lambda > 0$, and a (typically) small positive value is being added to the diagonal of $A^TA$. It is the modification of the diagonal that induces bias in the TLS and RR solutions relative to CLS. The exact relationships can be derived by substituting the CLS result into the other two expressions in Equation (6), then TLS: $x_{CLS} = (I - \sigma^2(A^TA)^{-1})x_{TLS}$ RR: $x_{CLS} = (I + \lambda(A^TA)^{-1})x_{RR}$ (7)

One particular consequence of Equation (7) is that:

$\|x_{RR}\|_2 < \|x_{CLS}\|_2 < \|x_{TLS}\|_2$ (8)

for non-zero values of the respective parameters. Thus, for an overall size fixed by the magnitude of the observations, RR would tend to decrease the spread of the parameters and TLS would increase the spread relative to the CLS result. Putting it in other terms, RR would tend to decrease the contrast among the components whereas TLS would tend to increase it. Given this insight, Equations (6) are seen to arise from a single least squares model that enables contrast bias to be introduced into the result. The normal equations formulation of the contrast-biased solution is:

$(A^TA + \gamma I)x = A^Tb$, $\gamma > -\sigma_{min}^2$ (9)

The restriction on $\gamma$ ensures that the biased cross product matrix $A^TA$ remains symmetric positive definite. Taking this restriction together with claims from the ridge regression literature suggests that useful values of the bias parameter $\gamma$ will fall in the range:

$-\sigma_{min}^2 < \gamma < \sigma_{max}^2$ higher contrast ⟵⟶ lower contrast (10)

Note that $\gamma = 0$ corresponds to the unbiased least squares solution. Equation (9) provides a biased least squares estimation of x given a single vector of observations b. Much like the unbiased estimator in Equation (4), however, it can be used to build up a biased ALS algorithm (BALS) that parallels Equation (3):

---

Make an initial guess for S
Do until converged:
    1. normalize S (11)
    2. select a bias parameter $\gamma_c$ 3. solve $\min_c \|S^TD^T - (S^TS + \gamma_c I)C^T\|_F$ subject to constraints on C 4. select a bias parameter $\gamma_s$ 5. solve $\min_s \|C^TD - (C^TC + \gamma_s I)S^T\|_F$ subject to constraints on S Compute $S = (I + \gamma_s(C^TC)^{-1})S$

---

Of course the roles of C and S can be interchanged whereby an initial guess is made for C and the order of the least squares solution steps 2 and 3 can be exchanged with steps 4 and 5. The subscript on $\gamma$ indicates the matrix for which we will be obtaining a biased estimate. As with Equation (3), the normalization step is important for stabilizing the iteration process. The final computation step is also important. It yields a final unbiased solution to ensure that the predicted signal intensity is comparable to the observed intensity.

The data matrix D can be preprocessed prior to the BALS analysis. For example, the data matrix can be a two-dimensional data matrix obtained by unfolding a measured multidimensional spectral data set. Furthermore, the data matrix can be weighted for heteroscedastic noise, as described in the above-referenced patents to Keenan and Kotula. Or, it can be a spatially compressed and/or spectrally compressed (e.g., a PCA-factored representation) data matrix, as described in U.S. patent application Ser. No. 10/772,548, filed Feb. 4, 2004 now U.S. Pat. No. 7,283,684, and U.S. patent application Ser. No. 10/772,805, filed Feb. 4, 2004 now U.S. Pat. No. 7,400,722, which are incorporated herein by reference.

Note also that, in general, the BALS algorithm of the present invention can be applied to the factorization of any arbitrary data matrix. That is, the data matrix D need not represent spectroscopic data and factor matrices C and S need not describe the concentrations and spectra of the spectroscopic data, respectively.

Just as it is the case with standard ridge regression, there are a variety of ways that the bias parameters might be selected in Equation (11). In fact, analogous to generalized ridge regression, there is no fundamental reason why $\gamma$ needs to be a scalar constant. $\gamma$ could be a diagonal matrix such that each variable is individually adjusted or biased. We might want to bias only a subset of variables, for instance. Such applications would certainly be problem dependent. Equation (10), however, suggests a generally useful way to select $\gamma$. Let f be a fractional number in the interval [0, 1) that expresses, in a qualitative way, the extent to which we wish to bias the results. f=0 would represent no bias with increasing f indicating increasing levels of bias. Then, in the language of component contrast, we would select $\gamma$ according to:

choose f to increase component contrast compute $\sigma_{min}^2$=smallest eigenvalue of $Z^TZ$ $$\gamma = -f\sigma_{min}^2 \qquad (12)$$

to decrease component contrast compute $\sigma_{max}^2$=largest eigenvalue of $Z^TZ$ $$\gamma = f\sigma_{max}^2$$

In this algorithm, Z is C or S, as appropriate. Thus, we have turned the problem of choosing a specific number into that of expressing a preference. f can be a user-adjustable parameter or can be chosen automatically. One possible automatic selection method will be discussed later.

Figure 7A:
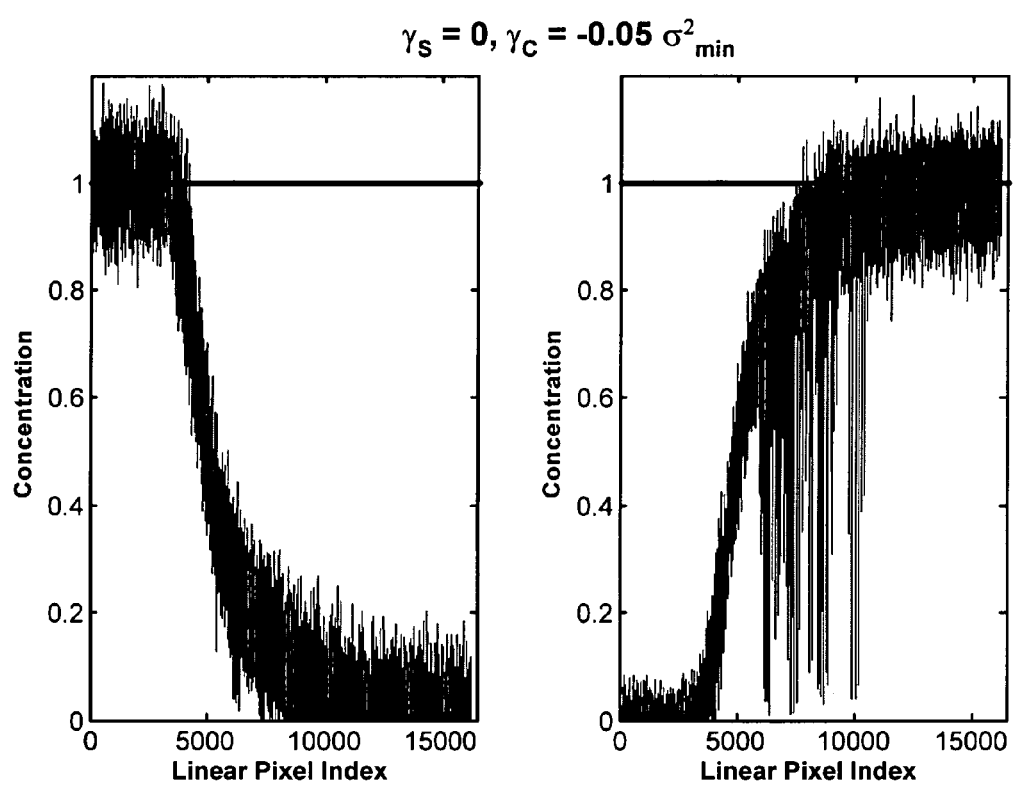
FIG. 7A shows the estimated concentrations, computed using a biased alternating least squares (BALS) algorithm with ($\gamma_S=0$, $\gamma_C=-0.05\sigma_{min}^2$ in) and subject to non-negativity constraints.
Figure 7B:
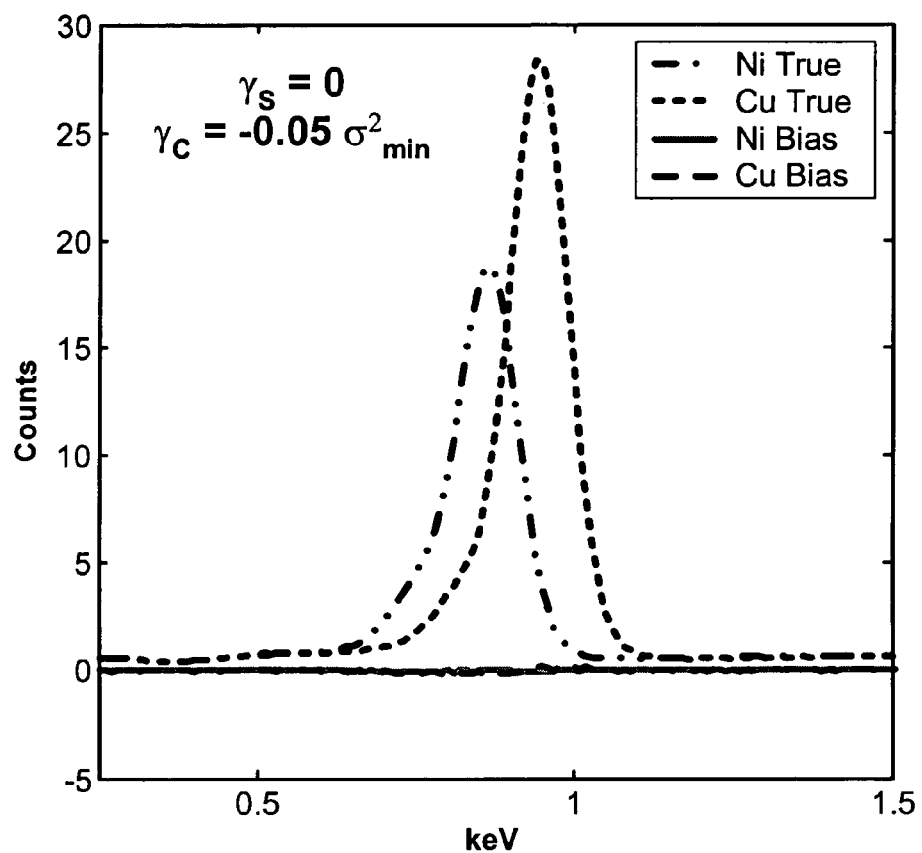
FIG. 7B shows the true pure component spectra and the bias introduced by the BALS estimation of the pure component spectra.
Figure 8A:
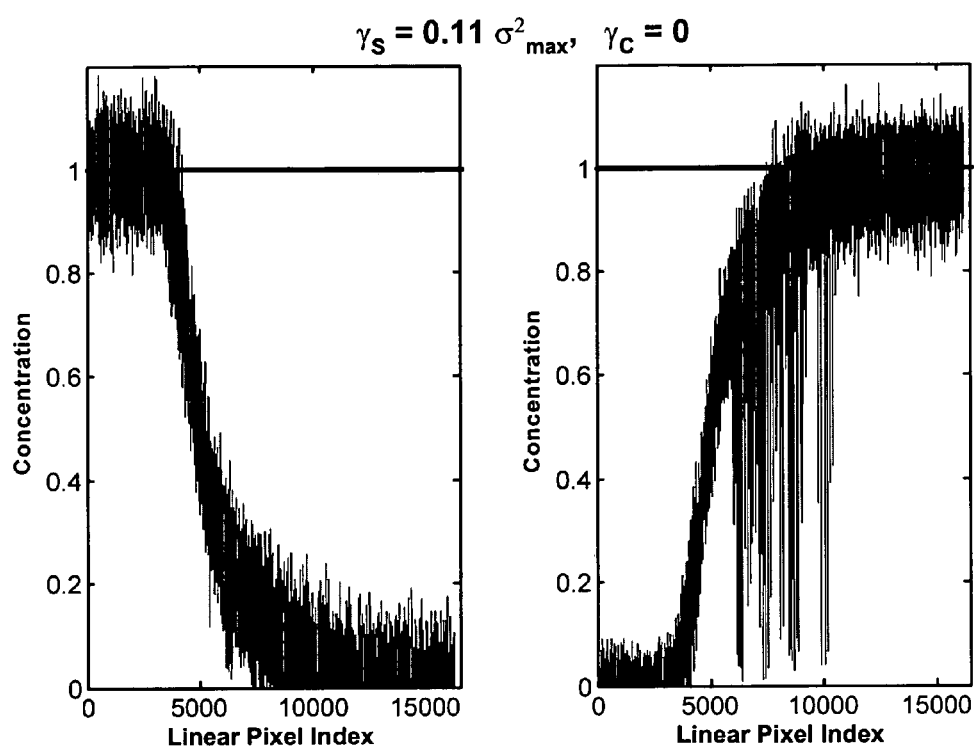
FIG. 8A shows the estimated concentrations, computed using a BALS algorithm with ($\gamma_S=0.11\sigma_{max}^2$, $\gamma_C=0$) and subject to non-negativity constraints.
Figure 8B:
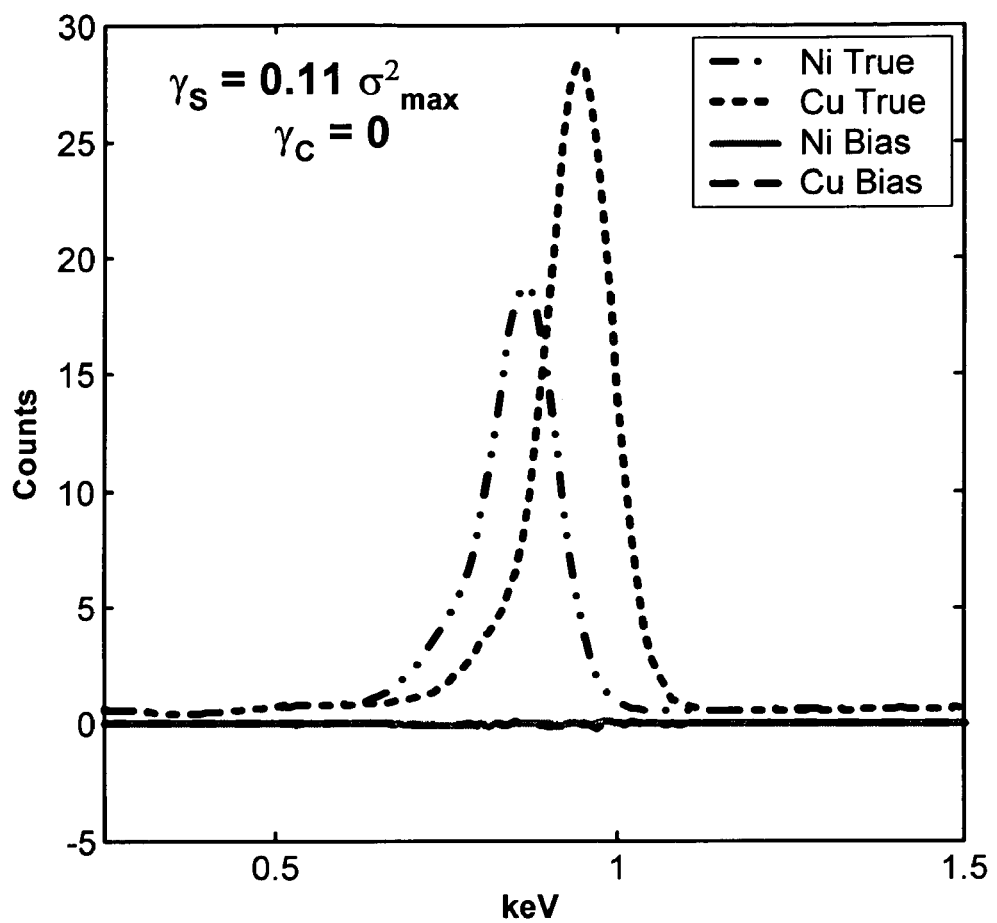
FIG. 8B shows the true pure component spectra and the bias introduced by the BALS estimation of the pure component spectra.

Returning to the Cu/Ni example, the constrained ALS analysis reduced compositional contrast and increased spectral contrast relative to the known true values. To correct for this, we can (1) increase compositional contrast by solving for the concentrations with $\gamma$<0; (2) decrease the spectral contrast by solving for the pure-component spectra using $\gamma$>0; or (3) do both. FIGS. 7A and 7B show the pure-component concentration and spectral estimates, respectively, after taking approach (1) and solving for the concentrations with ($\gamma_s$=0, $\gamma_c$=-0.05$\sigma_{min}^2$) and subject to non-negativity constraints. Bias in the pure spectral components is essentially eliminated and there is a residual bias of less than 1% in the estimated composition of the pure nickel and about 2% in the composition of pure copper. Solving for the pure component spectra according to approach (2) with ($\gamma_s$=0.11$\sigma_{max}^2$, $\gamma_c$=0) and subject to non-negativity constraints gave the results shown in FIGS. 8A and 8B. These results are essentially equivalent to those in FIGS. 7A and 7B.

Figure 9A:
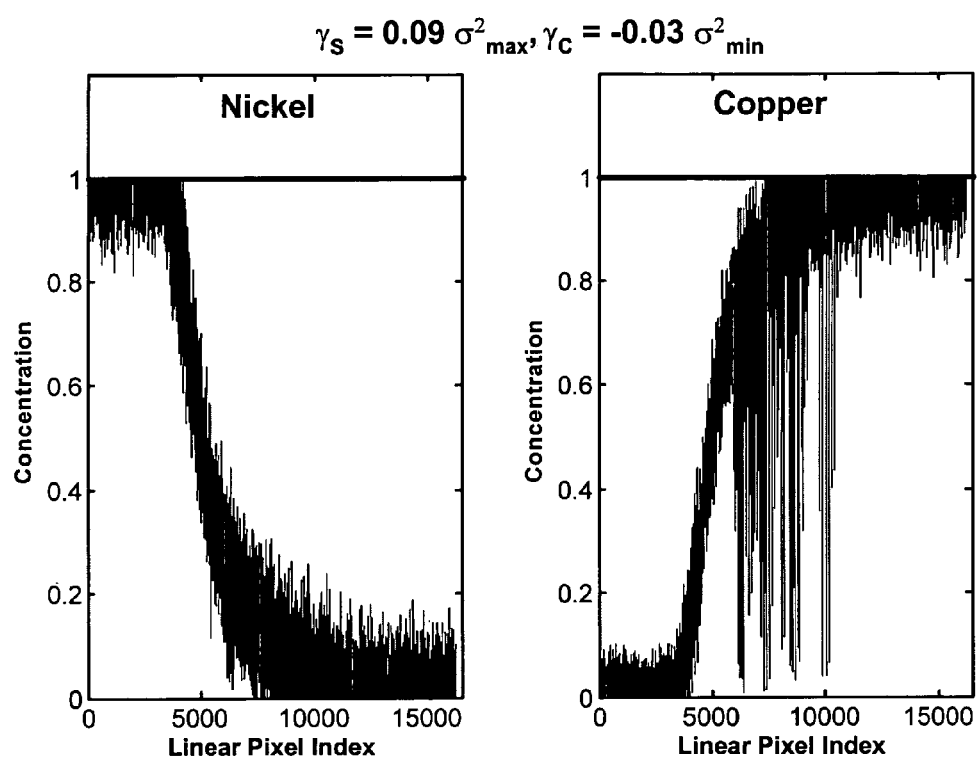
FIG. 9A shows the estimated concentrations, computed using a BALS algorithm with ($\gamma_S=0.09\sigma_{max}^2$, $\gamma_C=-0.03\sigma_{max}^2$) and the respective concentrations limited to the range of 0-1.
Figure 9B:
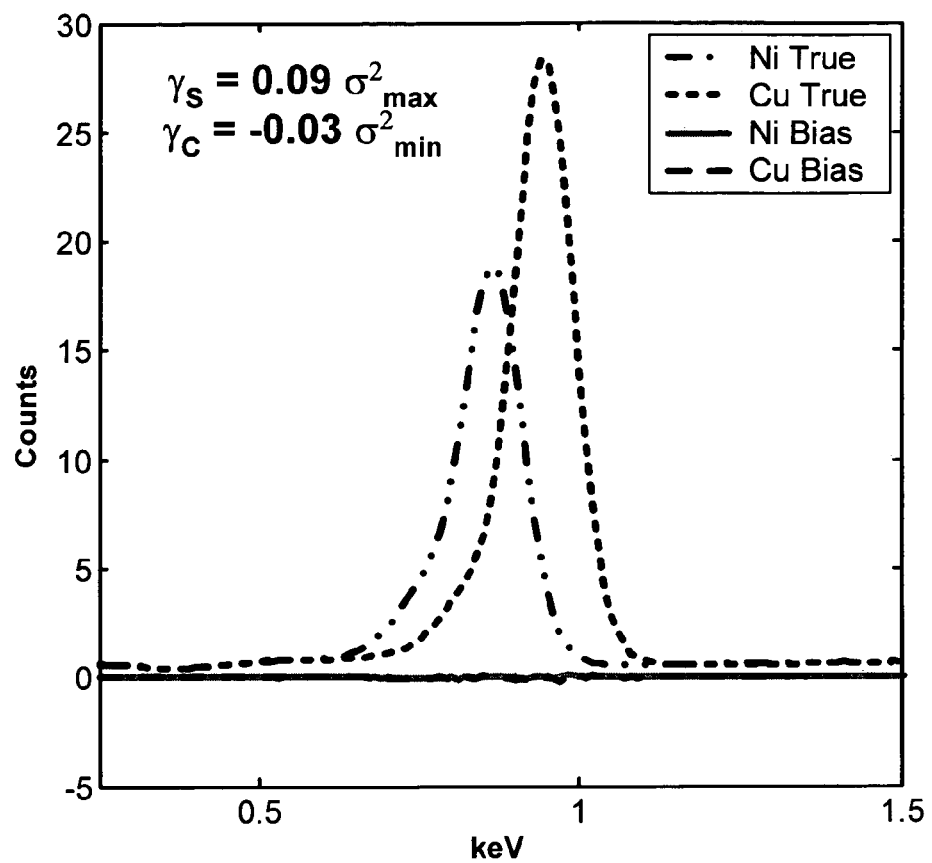
FIG. 9B shows the true pure component spectra and the bias introduced by the BALS estimation of the pure component spectra.

It should also be noted that the BALS algorithm is extremely general and the constraints in Equation (11) are not limited to non-negativity. For example, the constraints can comprise non-negativity constraints, general linear equality constraints, general linear inequality constraints, combined linear equality and inequality constraints, constraints imposed by the method of weighting, constraints imposed as "preferences" using the method of weighting, bounded variable constraints, simple variable equality constraints, closure constraints, or combinations of the above constraints. FIGS. 9A and 9B show the results obtained for the Cu/Ni example when the respective concentrations are limited to the range of 0-1 using, for instance, the Bounded Variables Least Squares (BVLS) algorithm in the C. L. Lawson et al. reference and approach (3) with ($\gamma_s$=0.09$\sigma_{max}^2$, $\gamma_c$=-0.03$\sigma_{min}^2$). Again, the results are quite similar to the other two approaches.

Figure 10:
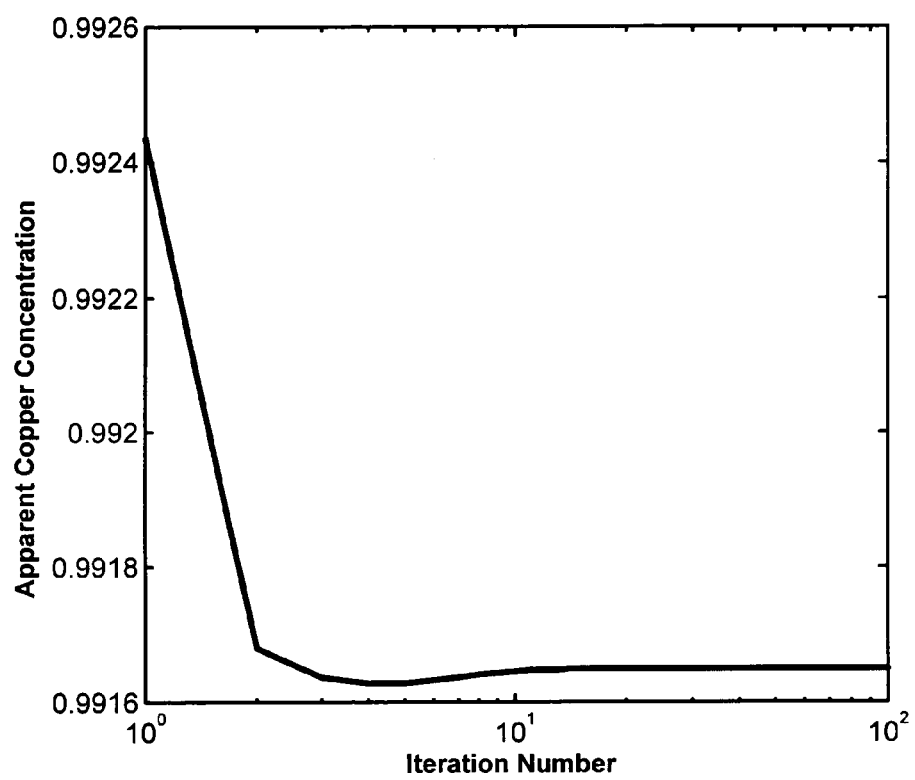
FIG. 10 shows the apparent mean copper concentration in the pure copper region as a function of the number of iterations, estimated using the non-negativity constrained BALS algorithm.

FIG. 10 shows the convergence behavior for the mean copper concentration in the pure copper pixels. Two things are noteworthy. First, the convergence is not monotonic, and this is true for the sum of squared residuals as well. The reason for this is that during the initial iterations, the eigenvalues of the spectral and concentration crossproduct matrices, hence the applied biases, are changing slightly. Second, and more importantly, while convergence required on the order of 10,000 iterations for standard ALS, the biased analyses converged to within machine precision within 50 iterations, thus yielding improved performance. It was recently reported that a similarly improved convergence rate was achieved by using ridge regression in a modified ALS algorithm. See J. H. Wang et al., "Application of modified alternating least squares regression to spectroscopic image analysis," *Analytica Chimica Acta* 476, 93 (2003).

Figure 11:
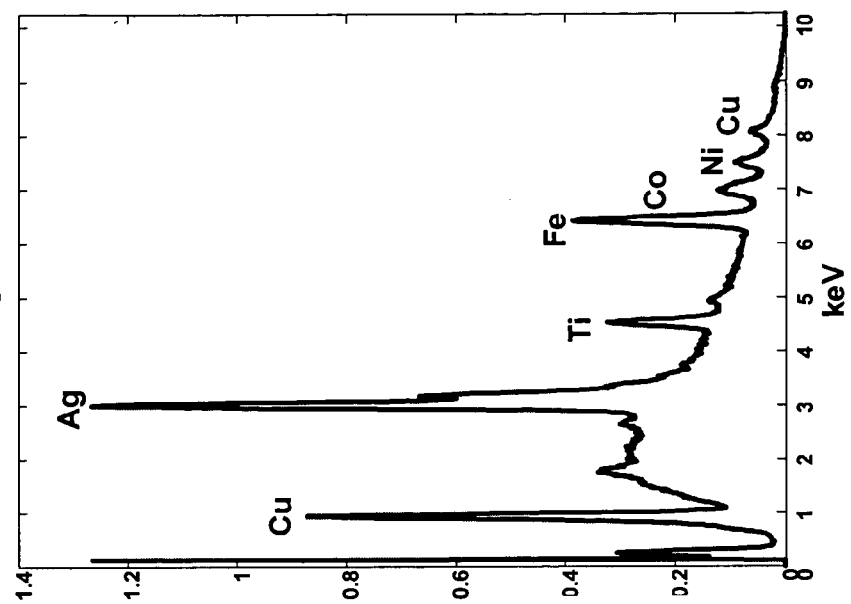
FIG. 11 shows a component image and the mean spectrum computed by EDS analysis of the interface between a copper/silver braze and an iron-nickel-cobalt alloy.
Figure 11:
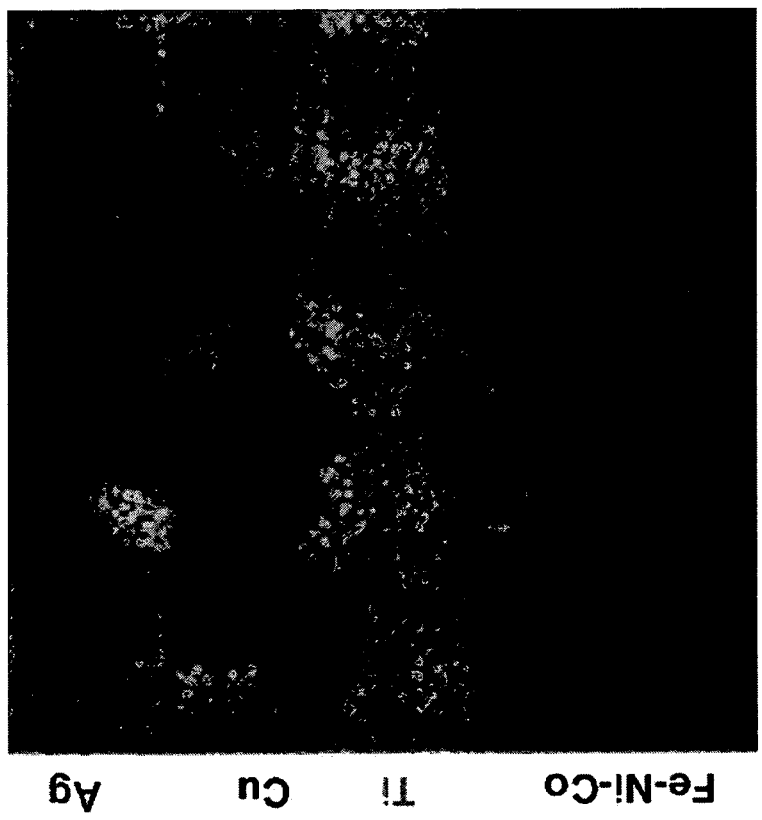

A second example problem is illustrated in FIG. 11. The sample represents an interface between a copper/silver braze and an iron-nickel-cobalt alloy, with titanium added to promote adhesion. The mean spectrum obtained by energy dispersive x-ray analysis is also shown in FIG. 11. In contrast with the Cu/Ni example, element-specific spectral features are not collinear; rather, the spectral features are collinear with a broad, non-specific background.

Figure 12:
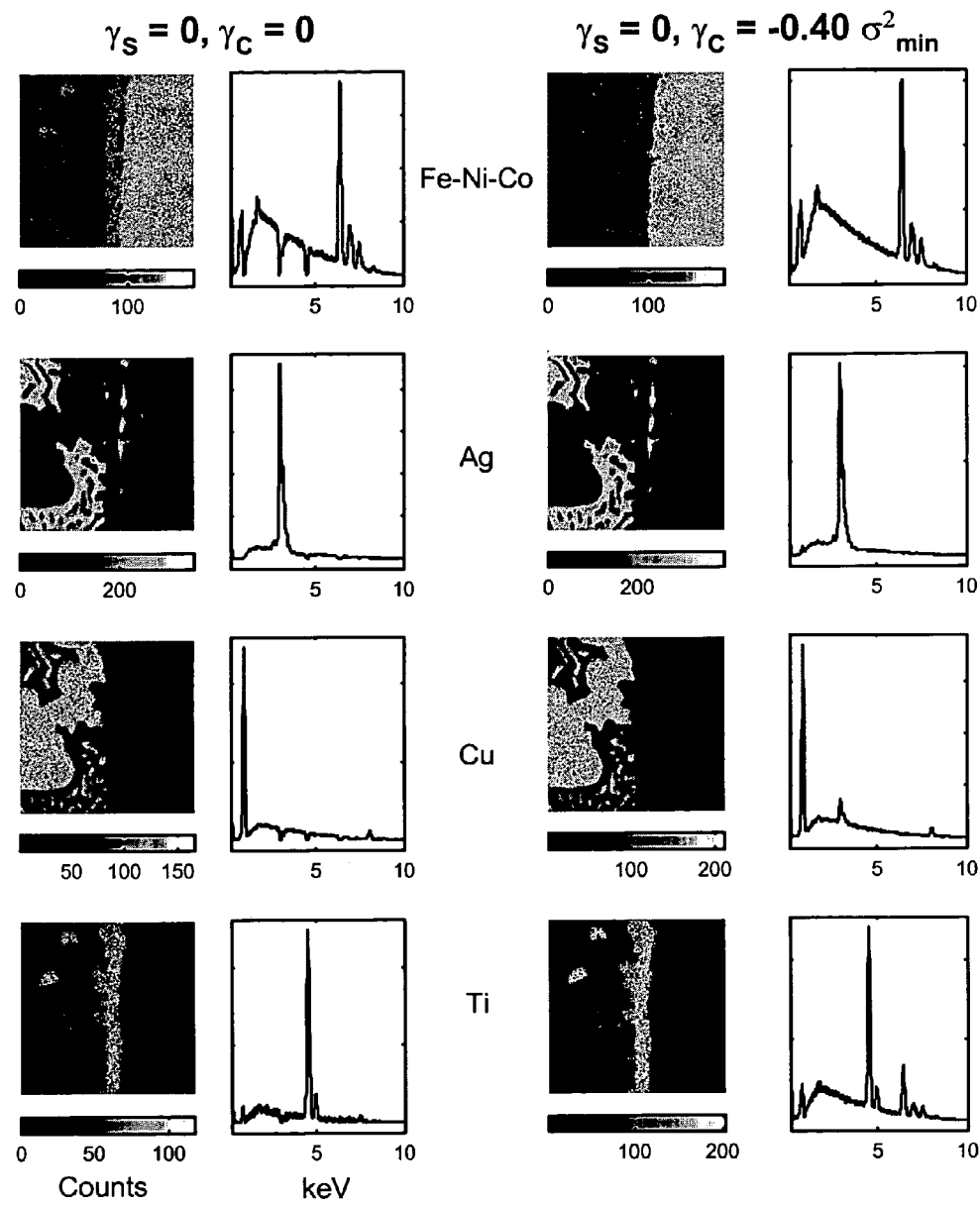
FIG. 12 shows the estimated concentration images and estimated pure component spectra for the braze interface, computed using the standard ALS algorithm ($\gamma_S=0$, $\gamma_C=0$) and the BALS algorithm with ($\gamma_S=0$, $\gamma_C=-0.40\sigma_{min}^2$) and with both algorithms subject to non-negativity constraints.

FIG. 12 compares standard ALS analysis ($\gamma_s$=0, $\gamma_c$=0) with the BALS analysis of the present invention, both subject to non-negativity constraints, for this example problem. The magnitude of the spectral bias in the ALS result is large, evidenced especially by the large negative-going features in the Fe—Ni—Co pure-component spectrum. Consequently, the compositions of the four phases appear to be substantially mixed. BALS analysis with ($\gamma_s$=0, $\gamma_c$=-0.40$\sigma_{min}^2$) eliminates the apparent spectral bias and the mixing of the compositions of the four phases.

The bias parameter needed to correct the braze example is larger than the corresponding parameter required for the Cu/Ni example, and the question arises as to how the parameters should be selected. One approach to selecting appropriate parameters for a given problem is simply trial and error. In general, the more ALS-induced bias that needs to be offset, the larger the bias parameter needs to be. Once the induced bias has been fully offset, however, further increases in the magnitude of the bias parameter have relatively little effect.

Figure 13:
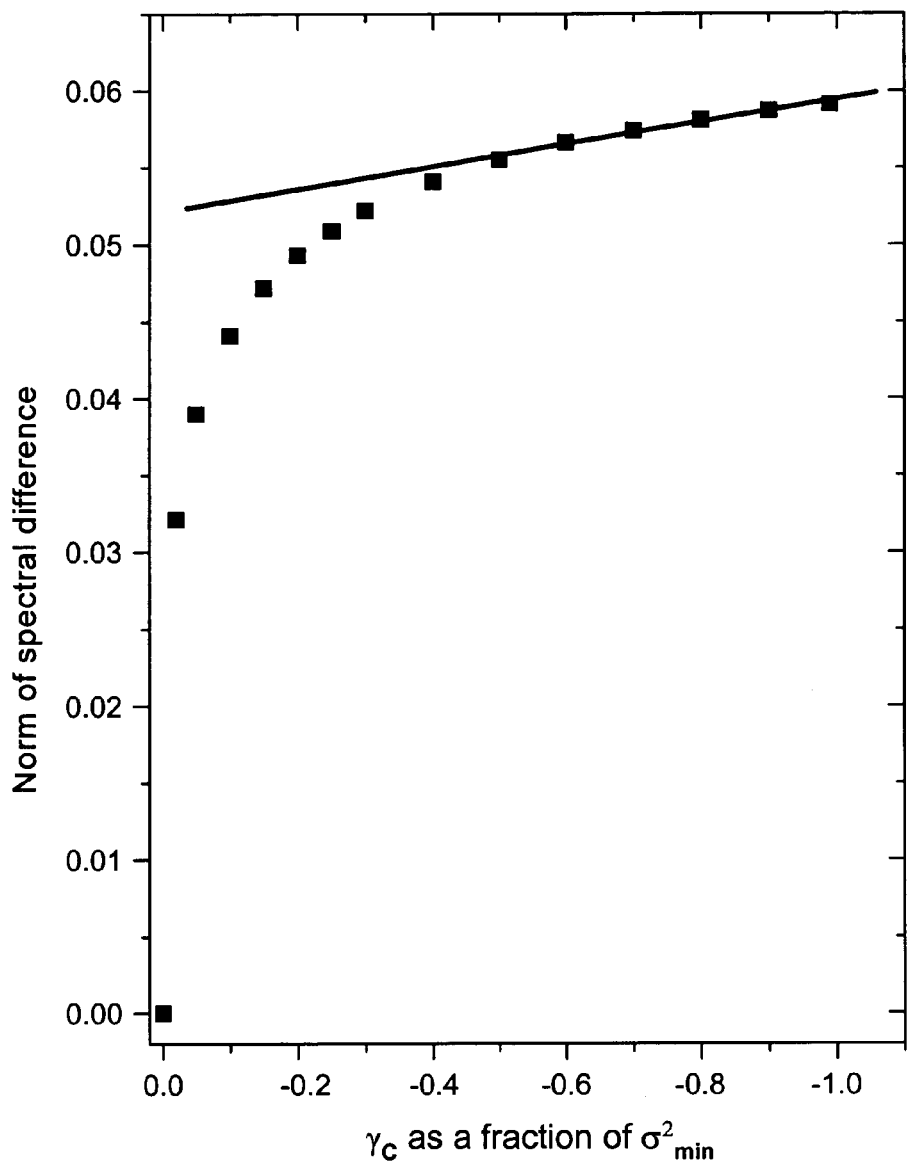
FIG. 13 shows the Frobenius norm of the spectral difference between the ALS- and BALS-derived pure components as a function of the bias parameter, $\gamma_C$.

This observation suggests another parameter selection approach as illustrated in FIG. 13 for the braze example. Given a metric describing how bias is changing, we simply look for the point at which increasing the bias parameter has little effect. In the present case, the metric is the Frobenius norm of the spectral difference between the ALS-derived pure components and those obtained from BALS with a given bias parameter. The break in the curve ($\gamma_c$≈-0.40$\sigma_{min}^2$) indicates the optimum parameter. Clearly, many other metrics might be used in a similar way depending on the particular problem at hand.

Exploiting Bias

A fundamental problem that arises from collinearity is that there will be a wide range of solutions that fit the data equally well. While these solutions may be equivalent mathematically, they may not have the same explanatory power for a given analytical problem. Introduction of bias selects some of the solutions as being preferable to others. Up to this point we have been concerned with offsetting bias introduced by the constraints in ALS. However, these methods can provide not only a bias adjustment, but a general way to control contrast in the extracted pure components.

Figure 14:
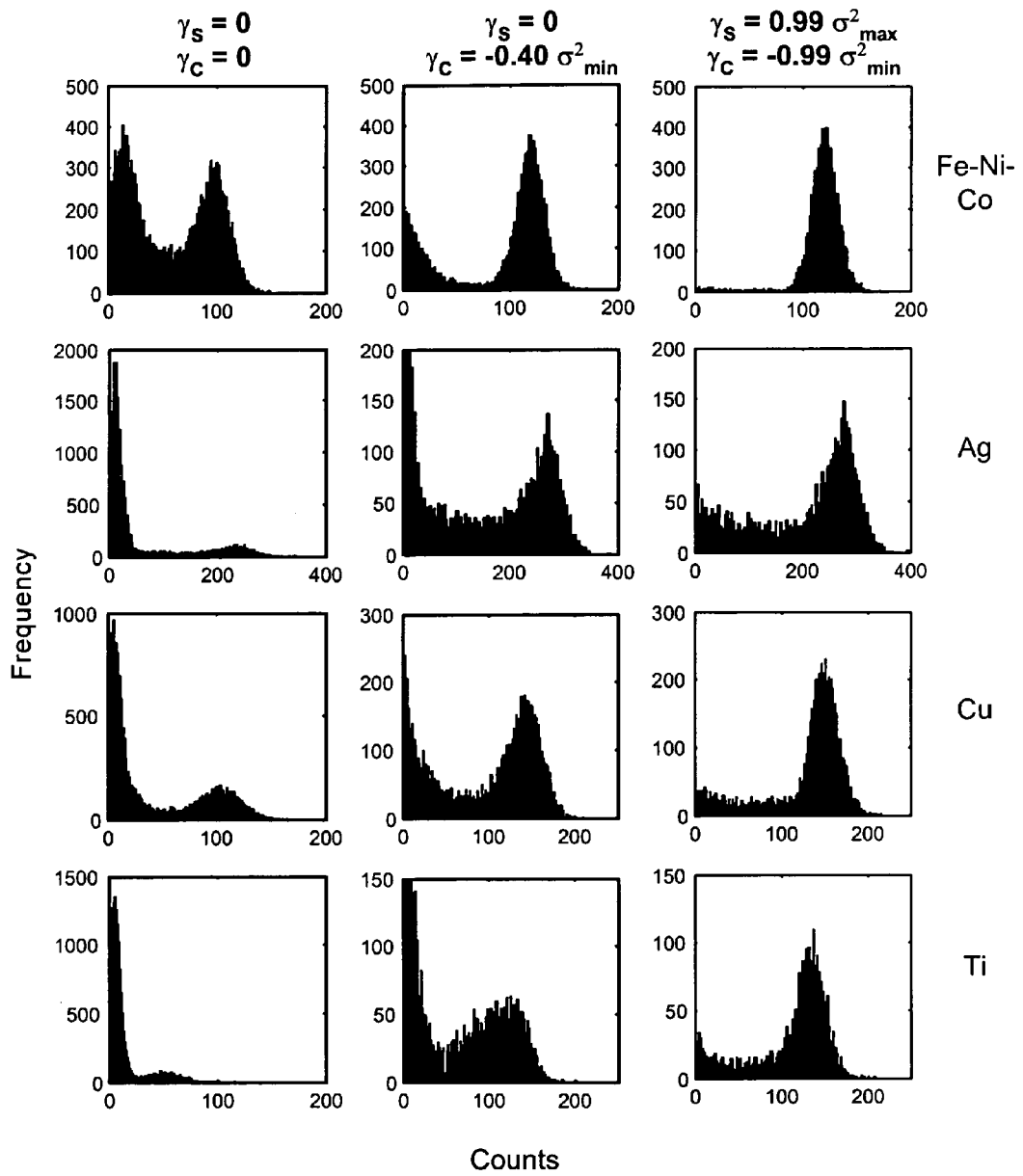
FIG. 14 shows the concentration histograms for the four components of the braze interface obtained by ALS ($\gamma_S=0$, $\gamma_C=0$), BALS with the "optimal" bias offset parameter ($\gamma_S=0$, $\gamma_C=-0.40\sigma_{min}^2$), and BALS with bias parameters selected to exaggerate spatial contrast ($\gamma_S=0.99\sigma_{max}^2$, $\gamma_C=-0.99\sigma_{min}^2$).

One example of when it would be useful to exaggerate contrast is when it is desired to segment an image into regions having some characteristics in common. Typically, thresholding techniques based on image intensity histograms are used for this purpose. See R. C. Gonzales et al., *Digital Signal Processing*, Prentice-Hall, Upper Saddle River, N.J. (2002). FIG. 14 compares concentration histograms for the four components of the braze example as obtained by ALS ($\gamma_S$=0, $\gamma_C$=0), BALS with the "optimal" bias offset parameter ($\gamma_S$=0, $\gamma_C$=−0.40$\sigma_{min}^2$), and BALS with bias parameters selected to exaggerate spatial contrast ($\gamma_S$=0.99$\sigma_{max}^2$, $\gamma_C$=−0.99$\sigma_{min}^2$). Clearly, the increase sharpness of the latter histograms will lead to a more successful segmentation of the spectral image by component.

Figure 15:
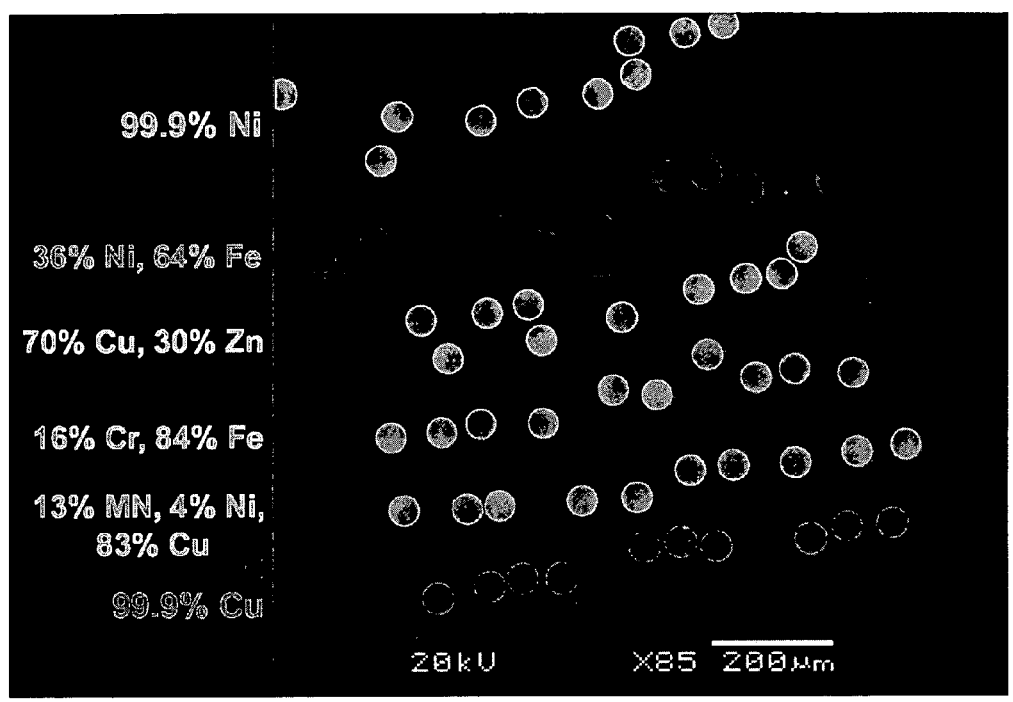
FIG. 15 shows a schematic illustration of the EDS images of six different alloy wires embedded in an epoxy block.

The example shown in FIG. 15 presents another interesting scenario where contrast adjustment can be used to good effect. The sample consists of 6 different alloy wires embedded in an epoxy block. The individual wires are composed from a palette of 6 different elements and the sample was imaged by energy dispersive x-ray analysis. We would expect the wires in this sample to be comprised of 6 pure components, but the presumed nature of the components may be ambiguous. It seems that there are two equally valid ways of viewing the components, either as alloys or as pure elements. Depending on the particular analytical question, one or the other of these views might be preferable.

Figure 16:
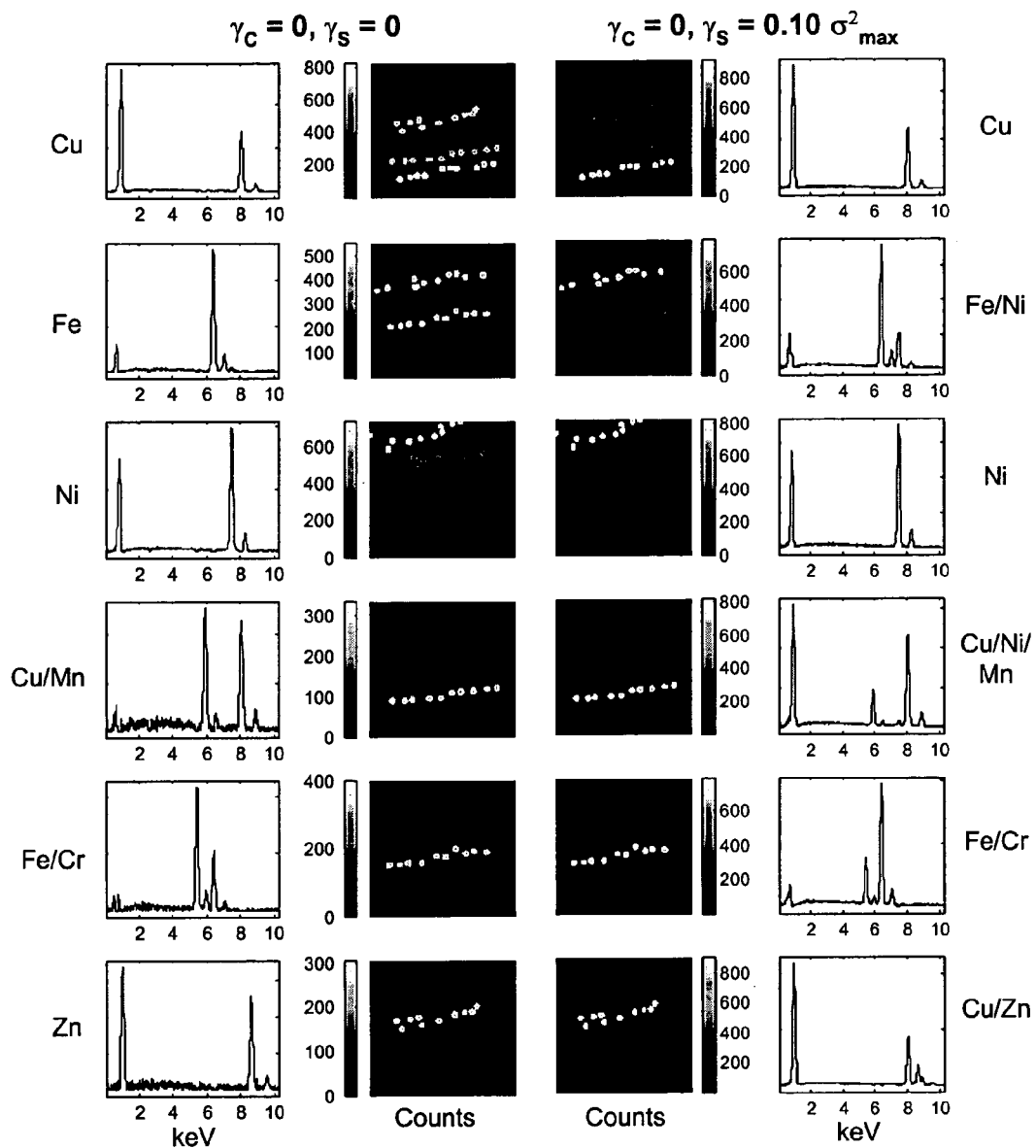
FIG. 16 shows the estimated concentration images and the estimated pure component spectra for the embedded alloy wires, computed by ALS ($\gamma_C=0$, $\gamma_S=0$) and BALS with ($\gamma_C=0$, $\gamma_S=0.10\sigma_{max}^2$) and with both algorithms subject to non-negativity constraints.

The left-hand panel in FIG. 16 shows the results of an ALS analysis ($\gamma_C$=0, $\gamma_S$=0). The results are, by and large, separated by element. The three wires containing copper are broken out in one component, the two containing iron in another component, and so on. This particular view is one that has high spectral contrast, i.e., the elemental spectra are highly orthogonal, and have relatively low spatial contrast, e.g. three different sets of wires show appreciable intensity in the copper component. The results of BALS analysis, where the bias parameters ($\gamma_C$=0, $\gamma_S$=0.10$\sigma_{max}^2$) have been selected to decrease spectral contrast, are shown in the right-hand panel in FIG. 16. The wires are now cleanly distinguished by alloy. Thus, using BALS enables the data to be understood from a variety of perspectives to aid in interpretation and analytical problem solving.

Connections with Other Work

For a positive bias parameter (i.e., ridge regression), the least squares problem that is being solved can be formulated as:

$$\min_x \left\| \begin{bmatrix} A \\ \lambda 1 \end{bmatrix} x - \begin{bmatrix} b \\ 0 \end{bmatrix} \right\| \tag{13}$$

A comparison with Chapter 22 in Lawson et al. shows that given large $\lambda$, this formulation is equivalent to solving an equality-constrained least squares problem by weighting, where all of the variables are constrained to be zero. A smaller value of the parameter, then, expresses a preference that the variables are small.

Recently, work has been published in which such preferences were used to make non-negativity a "soft" constraint. See P. J. Gemperline et al., "Advantages of soft versus hard constraints in self-modeling curve resolution problems," *Analytical Chemistry* 75(16), 4236 (2003). The basic idea is that by making non-negativity a preference, noisy components are allowed to go slightly negative. This is accomplished by using the weighting method to solve for the actively constrained variables in an active/passive set solution strategy. Mathematically, this is equivalent to replacing the identity matrix in Equation (13) by a selection matrix that selects the actively constrained variables. One difficulty with this approach is that the noise is still being treated asymmetrically. "Negative" noise will be damped but "positive" noise is still ignored. The BALS algorithm of the present invention, when combined with an active/passive set NNLS algorithm, effectively selects the passive variables in Equation (13). In other words, negative noise is completely eliminated and positive noise is damped.

Of course, the two approaches can be combined by giving different weights (i.e. bias parameters) to the active and passive variables. Given that $K_A$ is the p×k selection matrix that selects the k active variables and $K_P$ is the p×(p−k) selection matrix for the (p−k) passively constrained variables, then the biased, preference solution at each step in the iteration satisfies the normal equations:

$$(A^T A + \lambda^2 K_A K_A^T + \gamma K_P K_P^T) x = A^T b, \lambda \geq 0, \gamma > -\sigma_{min}^2$$

$$K_A K_A^T + K_P K_P^T = I \tag{14}$$

Figure 17:
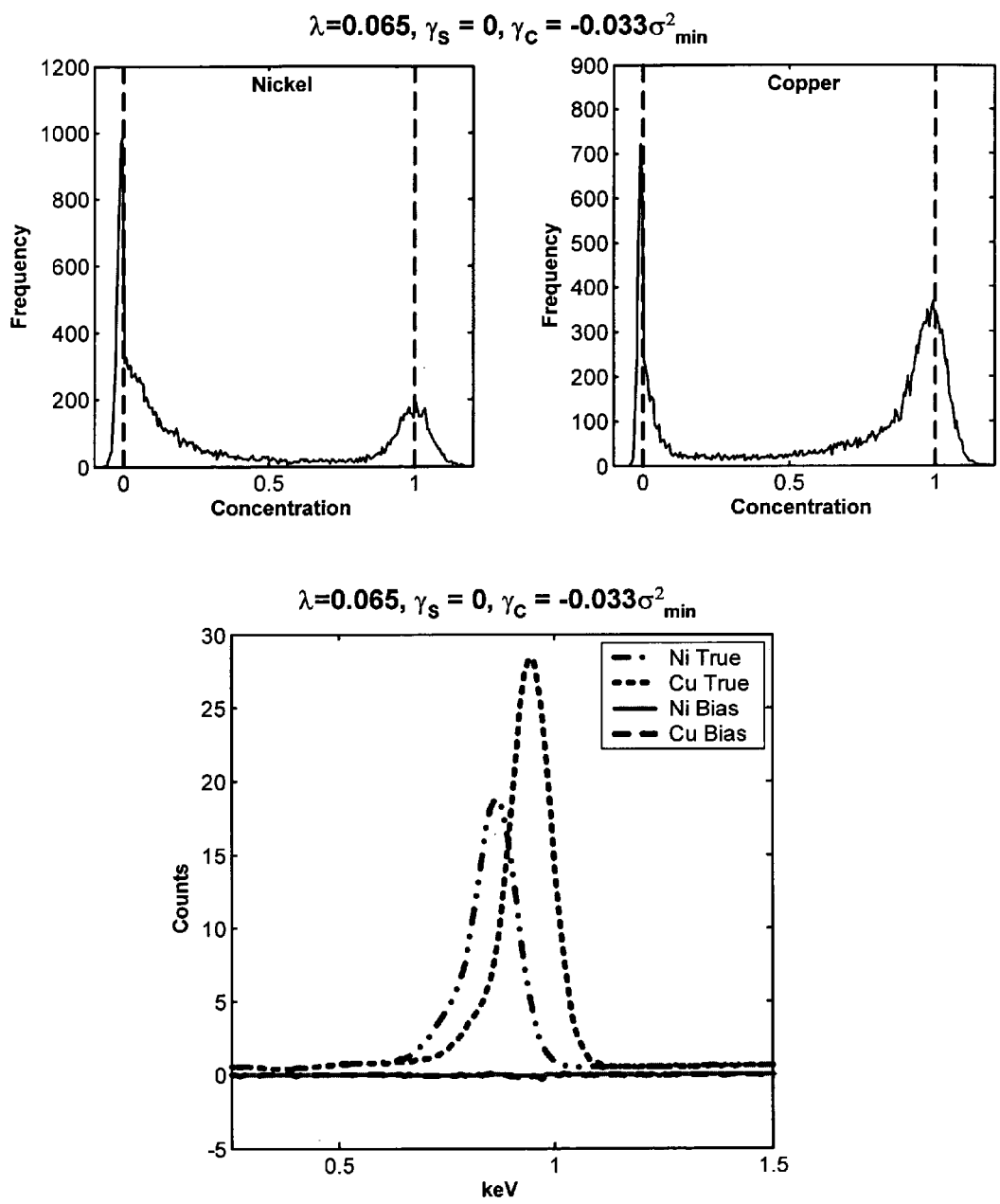
FIG. 17 shows BALS analysis results for the copper/nickel data set when the non-negativity constraints are imposed as preferences.

BALS analysis results for the copper/nickel data set when the non-negativity constraints are imposed as preferences are shown in FIG. 17. Spectral bias is largely eliminated, as is concentration bias. In the latter case, some concentrations are seen to be negative and the concentration histograms for the two components have maxima near the known pure element compositions.

A second related work was recently published in J.-H. Wang et al, "Application of modified alternating least squares regression to spectroscopic image analysis," *Analytica Chimica Acta* 476, 93 (2003). The authors employed ridge regression in a modified ALS algorithm (MALS) for the purpose of improving solution speed, stability and "component resolution ability." The improved convergence rate and stability is also observed with the BALS algorithm of the present invention, as described supra. A difference with the BALS algorithm is that the MALS algorithm takes explicit steps to avoid introducing any bias into the results, whereas, the BALS algorithm intentionally introduces bias. Additional differences are that positive ridge parameters are used in the computation of both the spectral and compositional parameters. This will tend to have a canceling effect. For instance, a positive ridge parameter when computing the spectra will tend to decrease the spectral contrast, a positive ridge parameter when computing the concentrations, on the other hand will tend to increase the spectral contrast.

General Linear Equality Constraints

The discussion surrounding Equation (4) considers the case where constrained least squares problems involving matrices of observations can be reformulated as a series of one-column-at-a-time problems. The specific example of the non-negativity constraint was considered there. A more generic notation to describe the general linearly constrained least squares model for a single vector of observations b is given by:

minimize $\|Ax-b\|_2^2$ subject to the constraints:

$Cx \geq d$ $Ex = f$ (15)

In this formulation, for example, the non-negativity constraint can be expressed with $C=I$, and $d=f=E=0$. The unconstrained solution x can be obtained by solving the normal equations:

$A^T A x = A^T b$ (16)

As shown by Equation (9), the present invention introduces bias into the solution vector by adding a diagonal matrix to the symmetric positive definite matrix $A^T A$. For the general linearly constrained least squares problem, the constraints can be applied through a symmetric modification of $A^T A$, yielding a new problem whose solution satisfies the constraints and which can be biased in a similar way. Returning, again, to the non-negativity constraint, each iteration of the solution process computes an unconstrained solution for the variables in the passive set. Given the selection matrix K introduced in Equation (5), the passive variables $\tilde{x}=K^T x$ satisfy the normal equations:

$(K^T A^T)(AK)(K^T x) = (AK)^T (AK)(K^T x) = (AK)^T b$ or $\tilde{A}^T \tilde{A} \tilde{x} = \tilde{A}^T b$ (17)

Clearly, the latter expression has the same form as Equation (16) and can be biased in a similar fashion. Exactly the same procedure can be used for other inequality constrained problems that are solved by the active/passive set strategy, for instance, the example shown in FIG. 9. where the constraints comprise both upper and lower bounds on the concentrations. For general linear inequality constraints, C. L. Lawson et al. shows how the solution procedure can be reduced to solving a non-negativity constrained problem. Thus, the algorithm outlined above is generally useful for solving inequality constrained problems.

One approach to solving general equality constrained least squares problems is the method of weighting which is outlined in Chapter 22 of C. L. Lawson et al. In brief, the unconstrained solution to the problem $$\min_{x} \left\| \begin{bmatrix} A \\ \lambda E \end{bmatrix} x - \begin{bmatrix} b \\ \lambda f \end{bmatrix} \right\|$$ (18)

converges to the solution to the equality constrained problem when the weighting parameter $\lambda$ becomes large (equality becomes a "preference" for smaller values of $\lambda$). The solution to Equation (18) satisfies the normal equations:

$(A^T A + \lambda^2 E^T E) x = A^T b + \lambda^2 E^T f$, $\lambda \geq 0$ (19)

Once again, this has the form of Equation (16) with a symmetric positive definite matrix multiplying x and the right hand side being a known constant. Bias can then be introduced in the usual way:

$(A^T A + \lambda^2 E^T E + \gamma I) x = A^T b + \lambda^2 E^T f$, $\lambda \geq 0$, $\gamma > -\sigma_{min}^2$ (20)

where $\sigma_{min}^2$ is now conveniently taken to be the smallest eigenvalue of $A^T A + \lambda^2 E^T E$. For the case of simple variable equality, $E^T$ becomes the p×k selection matrix that selects the k variables that are to be equality constrained. More general linear equality constraints, closure or the sum-to-one constraint, for instance, can also be easily handled by weighting.

Figure 18A:
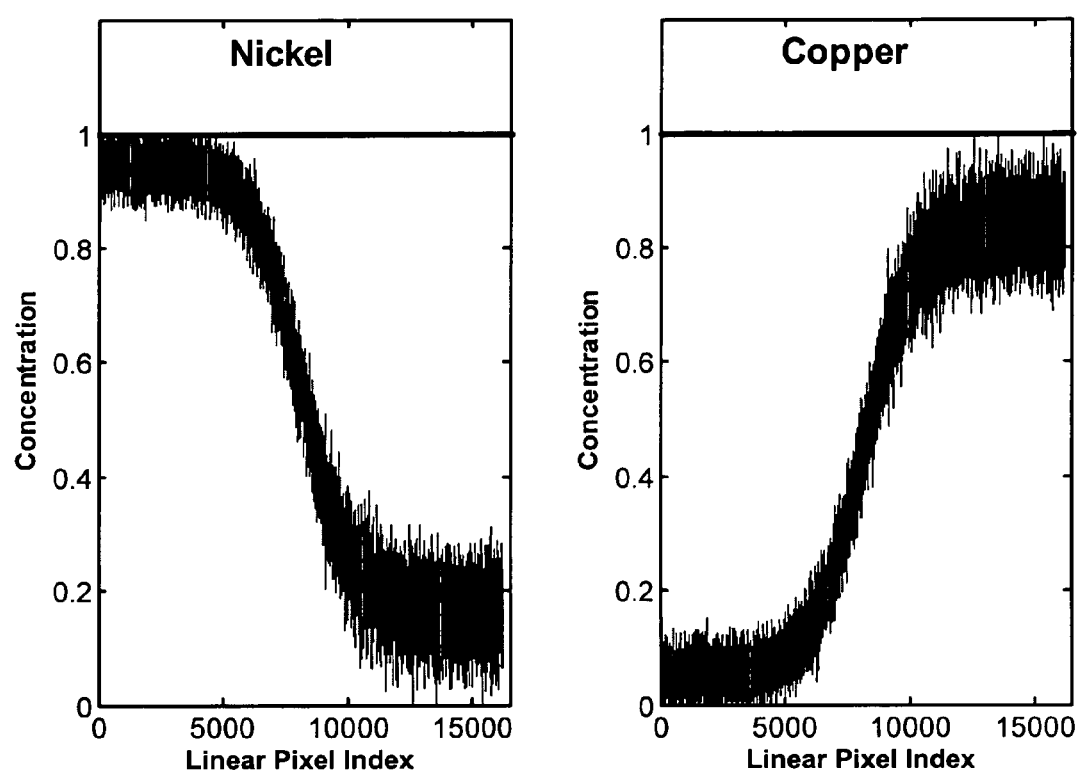
FIG. 18A shows the estimated concentrations of nickel and copper of a simulated data set, computed using an ALS analysis that incorporated both closure and non-negativity of the concentrations, plotted against a linear pixel index.
Figure 18B:
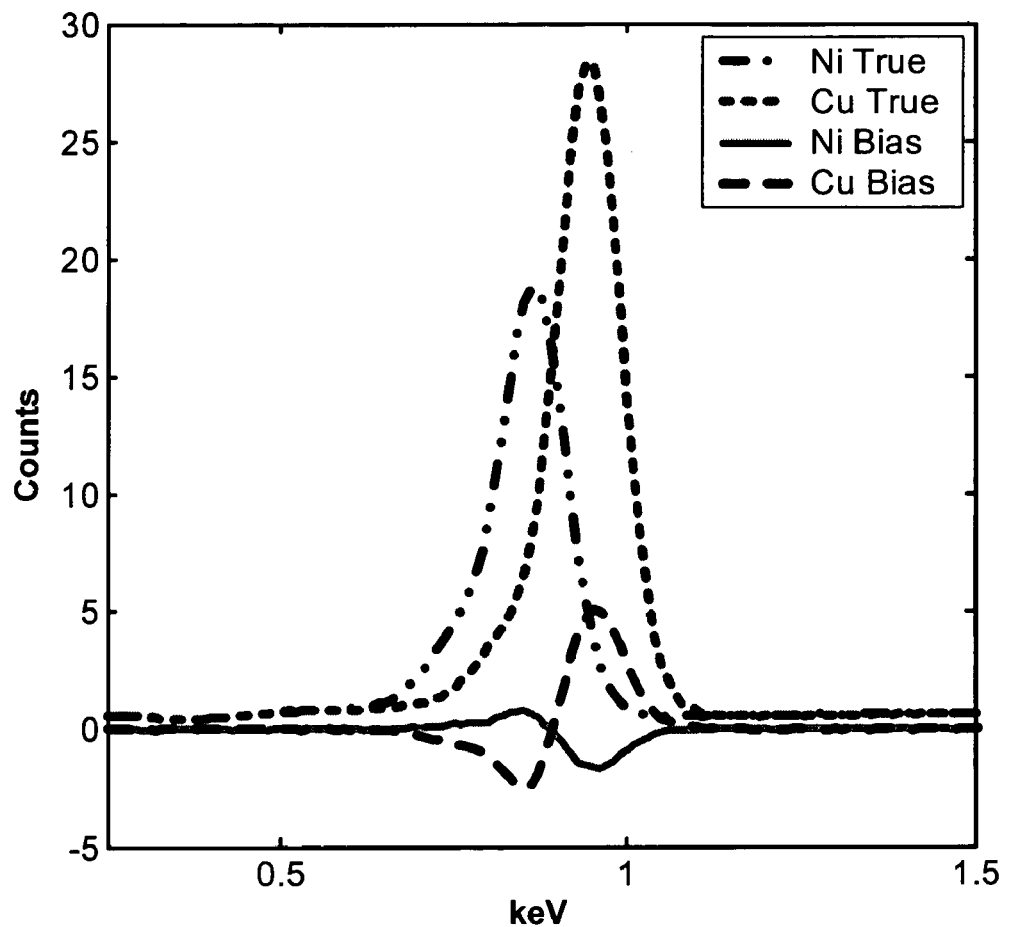
FIG. 18B shows the true pure component spectra and the bias introduced by the ALS analysis.
Figure 19A:
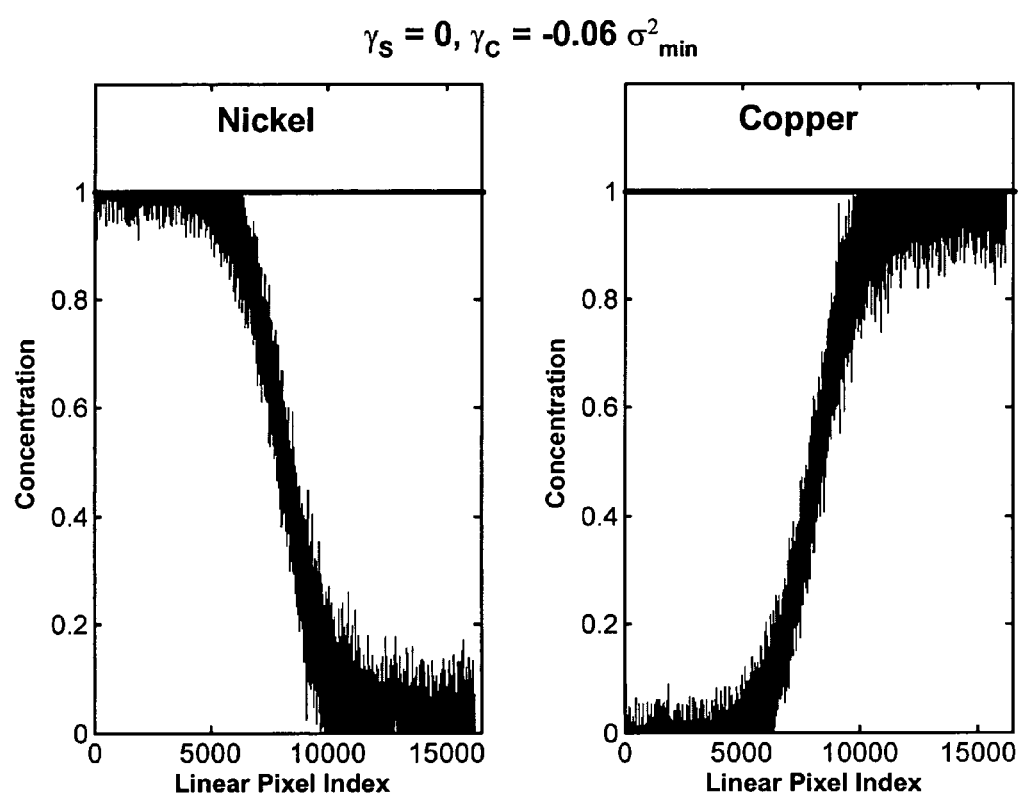
FIG. 19A shows the estimated concentrations of nickel and copper of the simulated data set, computed using a BALS analysis with bias parameters ($\gamma_S=0$, $\gamma_C=-0.06\sigma_{min}^2$) that incorporated both closure and non-negativity of the concentrations, plotted against a linear pixel index.
Figure 19B:
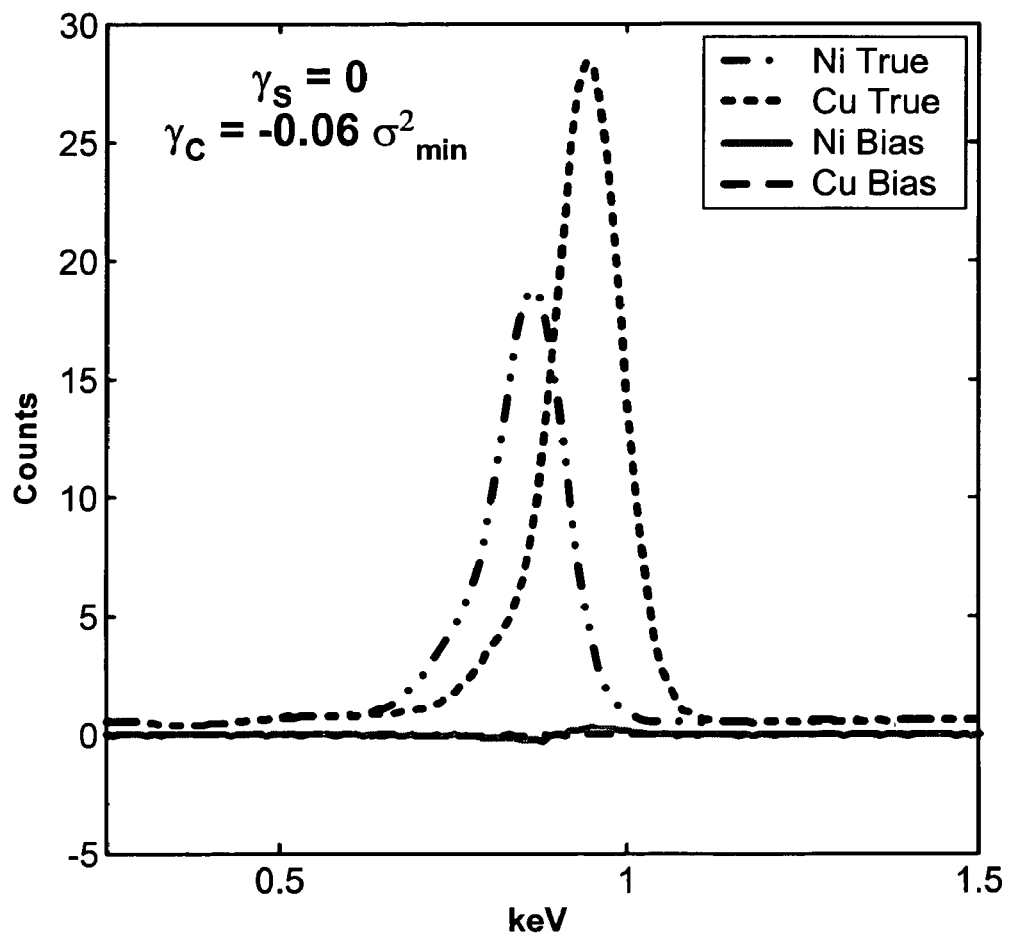
FIG. 19B shows the true pure component spectra and the bias introduced by the BALS analysis.

Finally, it should be clear that the active/passive set strategy outlined in Equation (17) can be used in conjunction with weighting to solve least squares problems containing both equality and inequality constraints using BALS. As a final example, consider the copper/nickel data set. In principle, the concentrations of copper and nickel should sum to one. Owing to the presence of voids in the sample, however, this constraint is not satisfied for all pixels. To demonstrate the BALS solution, then, a simulated data set created from the pure component spectra shown in FIG. 1 and using concentrations that rigorously sum to one was used. Noise was then added to the simulated spectra using a Poisson random number generator. FIGS. 18A and 18B show the results for an ALS analysis that incorporated both closure and non-negativity of the concentrations. Comparison with FIGS. 5A and 5B suggests that the bias in the result has increased owing to the additional constraint. The results of the BALS analysis using the same simulated data and constraint sets are shown in FIGS. 19A and 19B. Once again, both spectral and compositional biases have been effectively eliminated by the BALS analysis.

The present invention has been described as a method for exploiting bias in factor analysis using constrained alternating least squares algorithms. It will be understood that the above description is merely illustrative of the applications of the principles of the present invention, the scope of which is to be determined by the claims viewed in light of the specification. Other variants and modifications of the invention will be apparent to those of skill in the art.

I claim:

1. A method for analyzing a sample from measured spectral data by factoring a spectroscopic data matrix D, describing the measured spectral data, into the product of a factor matrix S, describing estimated spectra of pure components of the sample, and a factor matrix C, describing estimated concentrations of pure components of the sample, according to $D=CS^T$, the method comprising:

a) collecting measured spectral data from the sample with a spectrometer, whereby the measured spectral data is described by the spectroscopic data matrix D, b) making an initial guess for the factor matrix S, c) normalizing the factor matrix S, d) selecting a bias parameter $\gamma_C$ greater than $\sigma_{min}^2$, where $\sigma_{min}^2$ is the smallest eigenvalue of $S^T S$, e) solving $$\min_{C} \|S^T D^T - (S^T S + \gamma_C I) C^T\|_F,$$

subject to constraints on the factor matrix C, f) selecting a bias parameter $\gamma_S$ greater than $-\sigma_{min}^2$, where $\sigma_{min}^2$ in is the smallest eigenvalue of $C^T C$, g) solving $$\min_{S} \|C^T D^T - (C^T C + \gamma_S I) S^T\|_F,$$

subject to constraints on the factor matrix S, h) repeating steps c) thorough g) at least once, and i) computing $S=(I+\gamma_S(C^T C)^{-1})S$ to provide the factor matrix S.

2. The method of claim 1, wherein the data matrix D is preprocessed.

3. The method of claim 2, wherein the data matrix D is weighted.

4. The method of claim 2, wherein the data matrix D is spatially compressed.

5. The method of claim 2, wherein the data matrix D is spectrally compressed.

6. The method of claim 1, wherein the bias parameter $\gamma_C$ is a diagonal matrix comprising individually adjusted diagonal values.

7. The method of claim 1, wherein the bias parameter $\gamma_S$ is a diagonal matrix comprising individually adjusted diagonal values.

8. The method of claim 1, wherein the bias parameter $\gamma_C$ is less than $\sigma_{max}^2$, where $\sigma_{max}^2$ is the largest eigenvalue of $S^TS$.

9. The method of claim 1, wherein the bias parameter $\gamma_S$ is less than $\sigma_{max}^2$, where $\sigma_{max}^2$ is the largest eigenvalue of $C^TC$.

10. The method of claim 1, wherein the constraints on the factor matrix C are selected from the group consisting of non-negativity constraints, general linear equality constraints, general linear inequality constraints, combined linear equality and inequality constraints, constraints imposed by the method of weighting, constraints imposed as preferences using the method of weighting, bounded variable constraints, simple variable equality constraints, closure constraints, and combinations of the above constraints.

11. The method of claim 1, wherein the constraints on the factor matrix S are selected from the group consisting of non-negativity constraints, general linear equality constraints, general linear inequality constraints, combined linear equality and inequality constraints, constraints imposed by the method of weighting, constraints imposed as preferences using the method of weighting, bounded variable constraints, simple variable equality constraints, closure constraints, and combinations of the above constraints.

12. The method of claim 1, wherein step h) is repeated for a fixed number of iterations.

13. The method of claim 1, wherein step h) is repeated until the solutions for C in step e) and the solutions for S in step g) converge.

14. A method for analyzing a sample from measured spectral data by factoring a spectroscopic data matrix D, describing the measured spectral data, into the product of a factor matrix S, describing estimated spectra of pure components of the sample, and a factor matrix C, describing estimated concentrations of pure components of the sample, according to $D=CS^T$, the method comprising:

a) collecting measured spectral data from the sample with a spectrometer, whereby the measured spectral data is described by the spectroscopic data matrix D, b) making an initial guess for the factor matrix C, c) normalizing the factor matrix C, d) selecting a bias parameter $\gamma_S$ greater than $\sigma_{min}^2$, where $\sigma_{min}^2$ is the smallest eigenvalue of $C^TC$, e) solving $$\min_{S}\|C^TD^T - (C^TC + \gamma_S I)S^T\|_F,$$

subject to constraints on the factor matrix S, f) selecting a bias parameter $\gamma_C$ greater than $-\sigma_{min}^2$, where $\sigma_{min}^2$ is the smallest eigenvalue of $S^TS$, g) solving $$\min_{C}\|S^TD^T - (S^TS + \gamma_C I)C^T\|_F,$$

subject to constraints on the factor matrix C, h) repeating steps c) thorough g) at least once, and i) computing $C=(I+\gamma_C(S^TS)^{-1})C$ to provide the factor matrix C.

15. The method of claim 14, wherein the data matrix D is preprocessed.

16. The method of claim 15, wherein the data matrix D is weighted.

17. The method of claim 15, wherein the data matrix D is spatially compressed.

18. The method of claim 15, wherein the data matrix D is spectrally compressed.

19. The method of claim 14, wherein the bias parameter $\gamma_S$ is a diagonal matrix comprising individually adjusted diagonal values.

20. The method of claim 14, wherein the bias parameter $\gamma_C$ is a diagonal matrix comprising individually adjusted diagonal values.

21. The method of claim 14, wherein the bias parameter $\gamma_S$ is less than $\sigma_{max}^2$, where $\sigma_{max}^2$ is the largest eigenvalue of $C^TC$.

22. The method of claim 14, wherein the bias parameter $\gamma_C$ is less than $\sigma_{max}^2$, where $\sigma_{max}^2$ is the largest eigenvalue of $S^TS$.

23. The method of claim 14, wherein the constraints on the factor matrix S are selected from the group consisting of non-negativity constraints, general linear equality constraints, general linear inequality constraints, combined linear equality and inequality constraints, constraints imposed by the method of weighting, constraints imposed as preferences using the method of weighting, bounded variable constraints, simple variable equality constraints, closure constraints, and combinations of the above constraints.

24. The method of claim 14, wherein the constraints on the factor matrix C are selected from the group consisting of non-negativity constraints, general linear equality constraints, general linear inequality constraints, combined linear equality and inequality constraints, constraints imposed by the method of weighting, constraints imposed as preferences using the method of weighting, bounded variable constraints, simple variable equality constraints, closure constraints, and combinations of the above constraints.

25. The method of claim 14, wherein step h) is repeated for a fixed number of iterations.

26. The method of claim 14, wherein step h) is repeated until the solutions for S in step e) and the solutions for C in step g) converge.

* * * * *